(12) United States Patent
Ullrich, Jr. et al.

(10) Patent No.: US 12,653,696 B2
(45) Date of Patent: Jun. 16, 2026

(54) MODULAR ADJUSTABLE CORPECTOMY CAGE

(71) Applicant: TITAN SPINE, INC., Mequon, WI (US)

(72) Inventors: Peter F. Ullrich, Jr., Neenah, WI (US); Eric Kennedy, Wauwatosa, WI (US); Charles J. Turner, Milwaukee, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

(21) Appl. No.: 18/583,441

(22) Filed: Feb. 21, 2024

(65) Prior Publication Data

US 2024/0189111 A1 Jun. 13, 2024

Related U.S. Application Data

(60) Continuation of application No. 17/476,640, filed on Sep. 16, 2021, now Pat. No. 11,911,290, which is a
(Continued)

(51) Int. Cl.
*A61F 2/44* (2006.01)
*A61F 2/46* (2006.01)
(Continued)

(52) U.S. Cl.
CPC .......... *A61F 2/4465* (2013.01); *A61F 2/4455* (2013.01); *A61F 2/4611* (2013.01); *A61B 2017/0256* (2013.01); *A61F 2002/30224* (2013.01); *A61F 2002/30235* (2013.01); *A61F*

*2002/30261* (2013.01); *A61F 2002/30383* (2013.01); *A61F 2002/30481* (2013.01); *A61F 2002/30487* (2013.01);
(Continued)

(58) Field of Classification Search
CPC ...... A61F 2/442; A61F 2/4465; A61F 2/4611; A61F 2002/30601
See application file for complete search history.

(56) References Cited

U.S. PATENT DOCUMENTS

| | | |
|---|---|---|
| 661,089 A | 11/1900 | Tanner |
| 2,821,762 A | 2/1958 | Foose |
| (Continued) | | |

FOREIGN PATENT DOCUMENTS

| | | |
|---|---|---|
| EP | 2722022 A1 | 4/2014 |
| WO | 8909035 A1 | 10/1989 |
| (Continued) | | |

OTHER PUBLICATIONS

Japanese Office Action; JP Application No. 2020-542158; dated Dec. 1, 2022.
(Continued)

*Primary Examiner* — Nicholas J Plionis
(74) *Attorney, Agent, or Firm* — Fletcher Yoder, P.C.

(57) ABSTRACT

A system for use during surgical procedures. The system includes an implant and a tool. The implant combines a modular adjustable cage and a shim that locks the cage into position, after the cage has been adjusted to its final position and at its final height, in situ. The tool combines an expander and an inserter. A related method of using the system is also provided.

20 Claims, 21 Drawing Sheets

Related U.S. Application Data division of application No. 16/274,483, filed on Feb. 13, 2019, now Pat. No. 11,135,070.

(60) Provisional application No. 62/630,488, filed on Feb. 14, 2018.

(51) Int. Cl.
    *A61B 17/02*        (2006.01)
    *A61F 2/30*         (2006.01)

(52) U.S. Cl.
    CPC .............. *A61F 2002/30537* (2013.01); *A61F 2002/3055* (2013.01); *A61F 2002/30556* (2013.01); *A61F 2002/30593* (2013.01); *A61F 2002/30601* (2013.01); *A61F 2002/30604* (2013.01); *A61F 2002/30772* (2013.01); *A61F 2002/30828* (2013.01); *A61F 2/442* (2013.01); *A61F 2/447* (2013.01); *A61F 2/4603* (2013.01); *A61F 2002/4622* (2013.01); *A61F 2002/4628* (2013.01); *A61F 2/4637* (2013.01); *A61F 2220/0025* (2013.01)

(56) References Cited

U.S. PATENT DOCUMENTS

| | | | |
|---|---|---|---|
| 3,286,749 | A | 11/1966 | Learned |
| 3,995,371 | A | 12/1976 | O'Keefe |
| 4,060,114 | A | 11/1977 | Matsushima |
| 4,163,698 | A | 8/1979 | Kuo et al. |
| 4,865,303 | A | 9/1989 | Hall |
| 5,158,571 | A | 10/1992 | Picha |
| 5,391,422 | A | 2/1995 | Omori et al. |
| 5,443,514 | A | 8/1995 | Steffee |
| 6,342,055 | B1 * | 1/2002 | Eisermann ............... A61F 2/44 |
| | | | 606/291 |
| 6,436,102 | B1 | 8/2002 | Ralph et al. |
| 6,447,546 | B1 | 9/2002 | Bramlet et al. |
| 6,575,975 | B2 | 6/2003 | Brace et al. |
| 6,681,662 | B2 | 1/2004 | Blackston |
| 6,863,673 | B2 | 3/2005 | Gerbec et al. |
| 6,974,480 | B2 | 12/2005 | Messerli et al. |
| 6,981,975 | B2 | 1/2006 | Michelson |
| 7,056,321 | B2 | 6/2006 | Pagliuca et al. |
| 7,112,224 | B2 | 9/2006 | Liu et al. |
| 7,179,225 | B2 | 2/2007 | Shluzas et al. |
| D539,934 | S | 4/2007 | Blain |
| D541,940 | S | 5/2007 | Blain |
| 7,226,451 | B2 | 6/2007 | Shluzas et al. |
| D564,095 | S | 3/2008 | Blain |
| D566,276 | S | 4/2008 | Blain et al. |
| 7,410,501 | B2 | 8/2008 | Michelson |
| 7,445,640 | B2 | 11/2008 | Despres et al. |
| D599,019 | S | 8/2009 | Pimenta et al. |
| 7,615,078 | B2 | 11/2009 | White et al. |
| 7,645,232 | B2 | 1/2010 | Shluzas |
| 7,651,496 | B2 | 1/2010 | Keegan et al. |
| 7,655,012 | B2 | 2/2010 | DiPoto et al. |
| 7,658,739 | B2 | 2/2010 | Shluzas |
| 7,662,190 | B2 | 2/2010 | Steinemann et al. |
| 7,691,120 | B2 | 4/2010 | Shluzas et al. |
| 7,736,305 | B2 | 6/2010 | DiPoto |
| 7,744,612 | B2 | 6/2010 | Blain |
| 7,758,620 | B2 | 7/2010 | Porcher |
| 7,850,695 | B2 | 12/2010 | Pagliuca et al. |
| 7,976,464 | B2 | 7/2011 | Shluzas et al. |
| 7,998,172 | B2 | 8/2011 | Blain |
| 8,062,304 | B2 | 11/2011 | Blain et al. |
| 8,100,955 | B2 | 1/2012 | Blain et al. |
| 8,142,355 | B2 | 3/2012 | Blain et al. |
| 8,162,994 | B2 | 4/2012 | Gimbel et al. |
| 8,172,854 | B2 | 5/2012 | Blain et al. |
| 8,347,768 | B2 | 1/2013 | Witte |
| 8,353,913 | B2 | 1/2013 | Moskowitz et al. |
| 8,399,008 | B2 | 3/2013 | Webster et al. |
| 8,425,602 | B2 | 4/2013 | Guyer et al. |
| 8,523,930 | B2 | 9/2013 | Saunders et al. |
| 8,608,651 | B2 | 12/2013 | Shluzas |
| 8,702,762 | B2 | 4/2014 | Jacene et al. |
| 8,770,068 | B2 | 7/2014 | Witte |
| 8,864,785 | B2 | 10/2014 | Pagliuca et al. |
| 8,894,652 | B2 | 11/2014 | Seifert et al. |
| 8,979,749 | B2 | 3/2015 | Gorek et al. |
| 2001/0001315 | A1 | 5/2001 | Bates et al. |
| 2001/0039464 | A1 | 11/2001 | Hackauf |
| 2002/0188294 | A1 | 12/2002 | Couture et al. |
| 2003/0031984 | A1 | 2/2003 | Rusin et al. |
| 2003/0189114 | A1 | 10/2003 | Taylor et al. |
| 2004/0098131 | A1 | 5/2004 | Bryan et al. |
| 2004/0117019 | A1 | 6/2004 | Trieu et al. |
| 2004/0172129 | A1 | 9/2004 | Schafer et al. |
| 2005/0101950 | A1 | 5/2005 | Gough et al. |
| 2005/0131416 | A1 | 6/2005 | Jansen et al. |
| 2005/0251257 | A1 | 11/2005 | Mitchell et al. |
| 2006/0004453 | A1 | 1/2006 | Bartish et al. |
| 2006/0041313 | A1 | 2/2006 | Allard et al. |
| 2006/0095136 | A1 | 5/2006 | McLuen |
| 2006/0122701 | A1 | 6/2006 | Kiester |
| 2006/0265065 | A1 | 11/2006 | Bagga et al. |
| 2006/0287652 | A1 | 12/2006 | Lessig et al. |
| 2006/0293748 | A1 | 12/2006 | Alexander et al. |
| 2006/0293752 | A1 | 12/2006 | Moumene et al. |
| 2007/0062933 | A1 | 3/2007 | Weber |
| 2007/0093898 | A1 | 4/2007 | Schwab et al. |
| 2007/0118220 | A1 | 5/2007 | Liu et al. |
| 2007/0118223 | A1 | 5/2007 | Allard et al. |
| 2007/0118243 | A1 | 5/2007 | Schroeder et al. |
| 2007/0173938 | A1 | 7/2007 | Sweeney |
| 2007/0191958 | A1 | 8/2007 | Abdou |
| 2007/0213826 | A1 | 9/2007 | Smith et al. |
| 2007/0233248 | A1 | 10/2007 | Schwab et al. |
| 2007/0255408 | A1 | 11/2007 | Castleman et al. |
| 2007/0255414 | A1 | 11/2007 | Melkent et al. |
| 2007/0260320 | A1 | 11/2007 | Peterman et al. |
| 2007/0269475 | A1 | 11/2007 | Gil et al. |
| 2007/0270951 | A1 | 11/2007 | Davis et al. |
| 2007/0270956 | A1 | 11/2007 | Heinz |
| 2007/0270960 | A1 | 11/2007 | Bonin, Jr. et al. |
| 2007/0293949 | A1 | 12/2007 | Salerni et al. |
| 2008/0071380 | A1 | 3/2008 | Sweeney |
| 2008/0077171 | A1 | 3/2008 | Blain et al. |
| 2008/0154378 | A1 | 6/2008 | Pelo |
| 2008/0249569 | A1 * | 10/2008 | Waugh .................... A61F 2/447 |
| | | | 606/249 |
| 2008/0249622 | A1 | 10/2008 | Gray |
| 2008/0269764 | A1 | 10/2008 | Blain et al. |
| 2008/0275459 | A1 | 11/2008 | Dickinson et al. |
| 2008/0288071 | A1 * | 11/2008 | Biyani ...................... A61F 2/44 |
| | | | 623/17.11 |
| 2009/0005784 | A1 | 1/2009 | Blain et al. |
| 2009/0014243 | A1 | 1/2009 | Whigham |
| 2009/0024132 | A1 | 1/2009 | Blain et al. |
| 2009/0054988 | A1 | 2/2009 | Hess |
| 2009/0076613 | A1 | 3/2009 | Biedermann et al. |
| 2009/0076614 | A1 | 3/2009 | Arramon |
| 2009/0082819 | A1 | 3/2009 | Blain et al. |
| 2009/0204152 | A1 | 8/2009 | Blain |
| 2009/0259316 | A1 | 10/2009 | Ginn et al. |
| 2009/0265007 | A1 | 10/2009 | Colleran |
| 2010/0023057 | A1 | 1/2010 | Aeschlimann et al. |
| 2010/0057206 | A1 | 3/2010 | Duffield et al. |
| 2010/0076559 | A1 | 3/2010 | Bagga et al. |
| 2010/0121385 | A1 | 5/2010 | Blain et al. |
| 2010/0168798 | A1 | 7/2010 | Clineff et al. |
| 2010/0179594 | A1 * | 7/2010 | Theofilos .................. A61F 2/44 |
| | | | 606/247 |
| 2010/0274286 | A1 | 10/2010 | Blain et al. |
| 2010/0274358 | A1 | 10/2010 | Mueller et al. |
| 2011/0040301 | A1 | 2/2011 | Blain et al. |
| 2012/0078371 | A1 | 3/2012 | Gamache et al. |
| 2012/0095561 | A1 | 4/2012 | Voisard et al. |
| 2012/0123424 | A1 | 5/2012 | Blain et al. |
| 2012/0123548 | A1 | 5/2012 | Lynn et al. |

(56) References Cited

U.S. PATENT DOCUMENTS

| | | | |
|---|---|---|---|
| 2012/0143341 A1 | 6/2012 | Zipnick | |
| 2012/0149991 A1 | 6/2012 | Blain et al. | |
| 2012/0158056 A1 | 6/2012 | Blain | |
| 2012/0226356 A1 | 9/2012 | Hirschl | |
| 2012/0232664 A1 | 9/2012 | Ulrich, Jr. et al. | |
| 2012/0239151 A1 | 9/2012 | Ulrich, Jr. et al. | |
| 2012/0282454 A1 | 11/2012 | Jansen et al. | |
| 2013/0150968 A1 | 6/2013 | Dinville et al. | |
| 2013/0245767 A1 | 9/2013 | Lee et al. | |
| 2013/0268008 A1 | 10/2013 | McDonough et al. | |
| 2014/0114417 A1* | 4/2014 | Theofilos | A61F 2/4611 |
| | | | 623/17.16 |
| 2014/0277510 A1 | 9/2014 | Robinson et al. | |
| 2014/0309691 A1 | 10/2014 | Brown et al. | |
| 2015/0066146 A1 | 3/2015 | Laubert | |
| 2015/0073555 A1 | 3/2015 | To et al. | |
| 2016/0052162 A1 | 2/2016 | Colin et al. | |
| 2017/0172743 A1 | 6/2017 | Bonutti | |
| 2017/0239062 A1 | 8/2017 | Williams | |
| 2017/0239063 A1* | 8/2017 | Predick | A61F 2/447 |
| 2017/0290666 A1 | 10/2017 | Behzadi | |
| 2017/0312084 A1 | 11/2017 | Ferro et al. | |

FOREIGN PATENT DOCUMENTS

| | | | |
|---|---|---|---|
| WO | 01/28469 | A2 | 4/2001 |
| WO | 01/95838 | A1 | 12/2001 |
| WO | 03013396 | A1 | 2/2003 |
| WO | 2004/041131 | A2 | 5/2004 |
| WO | 2006/121795 | A2 | 11/2006 |
| WO | 2007/089905 | A2 | 8/2007 |
| WO | 2008065450 | A1 | 6/2008 |
| WO | 2008/103843 | A1 | 8/2008 |
| WO | 2009/006225 | A2 | 1/2009 |
| WO | 2009/029458 | A1 | 3/2009 |
| WO | 2009/140544 | A1 | 11/2009 |
| WO | 2010027359 | A1 | 3/2010 |
| WO | 2017/091657 | A1 | 6/2017 |
| WO | 2017/177046 | A1 | 10/2017 |

OTHER PUBLICATIONS

International Preliminary Report on Patentability received for PCT Patent Application No. PCT/US2019/017944, mailed on Aug. 27, 2020, 10 pages.

International Search Report and Written Opinion received for PCT Patent Application No. PCT/US2019/017944, mailed on May 13, 2019, 13 pages.

Petrini et al. "Biomedical Applications of Shape Memory Alloys", J. Metallurgy, vol. 2011, (2011)Article ID 501483 pp. 1-15.

Shellabear, M., et al., "DMLS-Development History and State of the Art", LANE Conference, 2004, Erlangen Germany.

Japanese Office Action; JP Application No. 2020-542158; dated Jun. 29, 2023.

* cited by examiner

300

310

300

310

310

300

310

301

660

670

662    664

666

668

500

668

500

668

670

700

622

440

680

460

682

480

MODULAR ADJUSTABLE CORPECTOMY CAGE

CROSS-REFERENCE TO RELATED APPLICATIONS

This application is a continuation of U.S. patent application Ser. No. 17/476,640, filed on Sep. 16, 2021, which is a divisional of U.S. patent application Ser. No. 16/274,483, filed on Feb. 13, 2019, which claims the benefit of U.S. Patent Application No. 62/630,488, filed on Feb. 14, 2018, and the entire disclosure of which is incorporated herein by reference.

FIELD OF THE INVENTION

The invention relates generally to interbody spinal implants and methods of using such implants and, in particular, to a modular adjustable corpectomy cage.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the vertebrae and discs may become diseased or infected, develop deformities such as tears and cracks, or simply lose structural integrity, for example bulge or flatten. These impaired vertebrae and discs can result in a lack of proper biomechanical support, and are often associated with chronic back pain.

Several surgical techniques have been developed to address spinal defects, such as vertebral or disc degeneration, deformity, or both. Spinal fusion has become a recognized surgical procedure for mitigating back and neck pain by restoring biomechanical and anatomical integrity to the spine. Spinal fusion techniques may involve the removal, or partial removal, of at least one intervertebral disc and preparation of the disc space for receiving an implant by shaping the exposed vertebral endplates. Such techniques may also involve removing all or part of the vertebral body located proximate the disc. An implant is then inserted.

A spinal implant may be inserted during a spinal fixation procedure using an anterior, lateral, posterior, or transverse spinal approach. A discectomy may be performed to remove or partially remove a defective or damaged intervertebral disc. The discectomy may create a space for one or more spinal implants. The amount of removed disc material may correspond to the size and type of the spinal implant or spinal implants to be inserted. A corpectomy is a surgical procedure that involves removing all or part of the vertebral body {in Latin called a "corpus vertebrae," hence the name corpectomy), usually as a way to decompress the spinal cord and nerves. A corpectomy is often performed in association with some form of discectomy.

Anterior interbody fusion procedures generally have reduced operative times, reduced blood loss, and do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This location is not the preferable seating position for an implant system, however, because only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence (defined as sinking or settling) into the softer cancellous bone of the vertebral body may arise from such improper seating.

In contrast, open ring-shaped cage implant systems are generally shaped to mimic the anatomical contour of the vertebral body. Traditional ring-shaped cages are generally comprised of allograft bone material, however, harvested from the human femur. Such allograft bone material restricts the usable size and shape of the resultant implant. For example, many of these femoral ring-shaped cages generally have a medial-lateral width of less than 25 mm. Therefore, these cages may not be of a sufficient size to contact the strong cortical bone, or apophyseal rim, of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Still further, other traditional non-allograft ring-shaped cage systems may be size-limited due to varied and complex supplemental implant instrumentation which may obstruct the disc space while requiring greater exposure of the operating space. These supplemental implant instrumentation systems also generally increase the instrument load upon the caretaker.

An implant system's corresponding surgical procedure, and the instruments used during such a procedure, should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Traditional interbody spinal implants generally do not seat properly on the preferred structural bone located near the apophyseal rim of the vertebral body, which is primarily composed of preferred dense subchondral bone. Accordingly, there is a need in the art for interbody spinal implants which better utilize the structurally supportive bone of the apophyseal rim. A related issue is that conventional implants are typically oversized relative to the space in which they are inserted to assure a tight fit in that space, and are inserted during spinal surgery by forcing (typically hammering) the implant into the desired position. Such hammering risks injury to the implant and, more important, to related anatomical features such as the spinal cord.

Spinal surgery is made complex, in part, by the proximity of the spinal cord, the cauda equina, or both. Preparation instruments and spinal implants may need to be carefully inserted to avoid damage to nerve tissue. Alignment and spacing of a spinal implant that is to be inserted into a patient may be determined before surgery. Achieving the predetermined alignment and spacing during surgery may be important to achieve optimal fusion of adjacent vertebrae.

The requirements of spinal surgery dictate that manufacturers provide implants of various footprints, and several heights in each footprint. This requirement means that the manufacturer needs to carry a significant amount of inventory of implants. Because there are so many different sizes of implants, there are setup costs involved in the manufacture of each different size. The result is increased implant costs, which the manufacturers pass along to the end users by charging high prices for spinal fusion implants.

Recently, adjustable fusion implants have been developed that allow the caretaker to adjust the height of the implant. Such height adjustment provides an ability to intra-operatively tailor the implant height to match the natural spacing between the vertebrae. In turn, this ability to tailor the implant height reduces the number of sizes that must be kept on hand to match the variable anatomy of the patients. In response, the medical field is replete with adjustable fusion implants that have an active mechanism for expanding the implant to change its height. An "active mechanism" is a mechanical structure built into the implant to cause the change in the height dimension.

For example, U.S. Pat. No. 6,863,673 issued to Gerbec et al. discloses a method for fusing two adjacent bones or pieces of bone. The method includes positioning an adjustable fusion implant between two adjacent bones or pieces of bone, the fusion implant having a first plate and an opposing second plate. The first plate has a rack or plurality of teeth; the second plate has a rack or plurality of corresponding teeth or holes. A portion of a tool inserted between the first plate and the second plate of the fusion implant is expanded so as to apply a separation force to the two plates and expand the fusion implant between the bones or pieces of bone. The force causes the teeth of the first plate to flex and either ride over the teeth on the second plate or pass from one hole in the second plate to the next; consequently, the implant can be selectively expanded in incremental amounts based on the spacing of the teeth (and holes). The tool is then removed from the expanded fusion implant.

The presence of the active mechanism significantly decreases the amount of internal space available for placement of bone graft and other osteogenic substances to encourage the bony fusion between the adjacent vertebrae. It would therefore be an improvement to provide an adjustable fusion implant that does not require the presence of an active mechanism, thereby maximizing the internal space for osteogenic substances and providing a better inducement for bony fusion.

Other adjustable fusion implants known in the art include components that must be pre-assembled before implantation. Therefore, it would be advantageous to provide a fusion implant that can be adjusted in situ. U.S. Patent Application Publication No. 2010/0076559 filed on behalf of Titan Spine, LLC, the owner of the subject application, discloses a composite telescoping interbody spinal implant and method of using the implant. Although it could be adjusted to a final position and fixed in that position before implantation, the telescoping design of the implant allows the implant to change in size while in position within the patient. The implant includes a cage formed of metal, a metal alloy, or both. The cage is able to change size following manufacture, and has a top plate with a plurality of posts and a bottom plate with a corresponding plurality of columns. The posts telescopically engage the columns upon assembly of the top plate with the bottom plate. The posts extend partially outside the columns when the top plate is in a raised first position with respect to the bottom plate; the posts and columns are fully engaged when the top plate is in a second position closest to the bottom plate. The implant also includes a non-metallic body inserted between the top plate and the bottom plate and defining the adjustable height of the implant.

Although many systems and methods have been suggested, the conventional implant systems and insertion methods fail to provide implants, instrumentation, and methods that allow the implant to be easily inserted to its final desired position, and expanded once positioned, within the disc space. During a cervical corpectomy procedure, one or more vertebral bodies are either wholly or partially removed. When the implant is placed between the adjacent endplates it spans over an exposed spinal cord, thus increasing the risk of injury if the implant were to migrate too far posterior. It is therefore important to be able to insert a smaller-than-nominal implant and expand the implant to the correct height in situ. It is also important to remove the need for hammering inherent when inserting a nominal-size implant.

In addition, because it must span multiple levels, the implant must be made available in a large range of sizes. This creates a burden logistically to manufacture, transport, and provide all options to the caretaker. Therefore, it is also important to be able to provide a relatively small number of components that can be assembled to create all the necessary combinations of final heights. An implant would also be desirable that can be continuously (rather than incrementally) expanded in situ, assuming a potentially infinite number of possible heights between a starting height and an upper limit.

Given the complexities of spinal surgery, a need exists for a spinal implant and associated instrument and method of use that improve the ease with which the implant may be manipulated during insertion or once within the disc space. Because safety, patient health, recovery speed, and reduced trauma are always surgical concerns, another need is to keep the insertion width required by the implant and instrument small. Another need is to allow the caretaker to manipulate the implant, using the instrument, within the disc space, in situ, without passing multiple instruments past the exposed nerve roots. A related need is to avoid or at least minimize the risk of trauma to the spine, as well as reduce the risk of damaging the nerve root with multiple passes of instrumentation.

SUMMARY OF THE INVENTION

To meet these and other needs, and in view of its purposes, the present invention provides a system for use during surgical procedures. The system includes an implant and a tool. The implant has a modular cage and a shim with a tool holding feature, an upper bracket, and a lower bracket. The modular cage includes four modules: (i) a first endplate adapted to press against anatomical structures of the patient, (ii) a second endplate adapted to press against opposing anatomical structures of the patient, (iii) a body with a top surface on which the first endplate is positioned and a track which engages the upper bracket of the shim and guides the shim into engagement with the modular cage, and (iv) a column with a top surface on which the second endplate is positioned, a track which engages the lower bracket of the shim and guides the shim into engagement with the modular cage, and at least one leg over which the body slides so that the at least one leg is contained at least partially within the body.

The tool has an expander and an inserter. The tool engages a tool holding feature on the modular cage and positions the modular cage at a surgical site within the patient. The expander slides the body along the at least one leg to separate the body from the column continuously in situ and thereby define the height of the implant. The inserter positions the shim between the body and the column. The height of the implant can be adjusted in situ to a potentially infinite number of possible heights between a starting height where the body is fully seated on the column and an upper limit where the body exceeds the height of the at least one leg. When positioned between the body and the column, the shim fixes the distance between the body and the column.

A related method of using the system is also provided. The method follows, or may include the steps of, identification of a spinal disc in need of repair or replacement, performance of at least a partial discectomy to create a disc space, and selection of the appropriate size of implant for the disc space. The method includes the following steps.

The caretaker first collects the modular components, including a first endplate, a body, a column, and a second endplate, that will form a modular cage of the implant having a size and shape suitable for the disc space created by the discectomy. The caretaker assembles the modular components to form the modular cage, with the body sliding over at least one leg of the column so that the at least one leg is contained entirely within the body. Optionally, bone graft material is inserted into an internal cavity defined by the modular cage. The caretaker uses the tool to insert the modular cage, without distracting the adjacent vertebral bodies, into the disc space created during the discectomy. The height of the modular cage is adjusted, using the tool, by sliding the body along the at least one leg of the column to separate the body from the column continuously in situ and thereby define the height of the implant, wherein the height of the implant is adjusted in situ to a potentially infinite number of possible heights between a starting height where the body is fully seated on the column and an upper limit where the body exceeds the height of the at least one leg.

The caretaker then selects a suitably sized shim and inserts the shim of the implant, using the tool, into the disc space and into engagement with the modular cage between the body and the column to fix the distance between the body and the column. The caretaker then releases the shim and the modular cage from the tool. Finally, the caretaker removes the tool from the disc space, leaving the implant in position within the patient.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Various terms relating to aspects of the present disclosure are used throughout the specification and claims. Such terms are to be given their ordinary meaning in the art unless otherwise indicated. Other specifically defined terms are to be construed in a manner consistent with the definition provided in this document.

As used throughout, the singular forms "a," "an," and "the" include plural referents unless expressly stated otherwise. A "patient" may be any animal, including mammals such as companion animals, laboratory animals, and non-human primates. Human beings are preferred. A functional spinal unit includes a vertebrae and the intervertebral discs between a superior and inferior vertebrae. A functional spinal unit may include a cervical functional spinal unit, a thoracic functional spinal unit, or a lumbar functional spinal unit.

Figures 1, 2A, 2B, 2C:
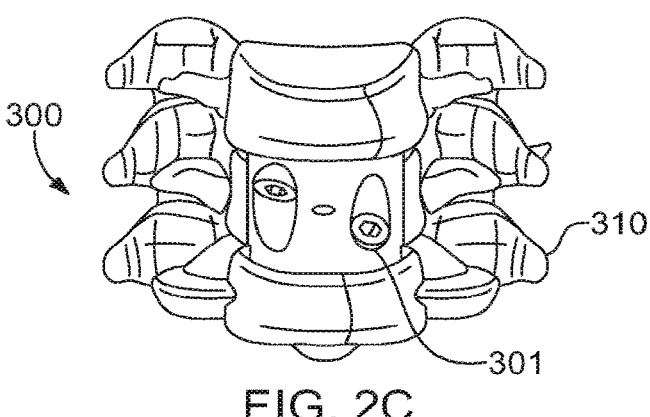
FIG. 1 shows a representation of a functional spinal unit.
FIG. 2A shows an anterior view of a partial corpectomy of a vertebrae.
FIG. 2B shows a perspective view of a partial corpectomy of a vertebrae with a portion of the vertebral endplate removed.
FIG. 2C shows an implant inserted into the channel of the vertebrae.

Referring now to the drawing, in which like reference numbers refer to like elements throughout the various figures that comprise the drawing, implants in accordance with certain aspects of the disclosure stand in the place of at least a portion of at least one vertebrae, including in the place of a functional spinal unit 300 which is illustrated in FIG. 1. The implants are preferably used in accordance with surgical procedures, as illustrated in FIG. 2A and FIG. 2B, that retain some portion of a vertebrae 310. FIG. 2A shows an anterior view of a partial corpectomy of a vertebrae 310, and FIG. 2B shows a perspective view of a partial corpectomy of a vertebrae 310 with a portion of the vertebral endplate removed. Such surgical procedures allow the implant to be seated in place of the removed portion and contact the extant bone, while the top and bottom surfaces of the implant contact the inferior and superior surfaces of adjacent vertebrae 310, including vertebral endplate bone. FIG. 2C shows an implant 301 inserted into the channel of the vertebrae 310.

Implants in accordance with certain aspects of the invention can be preferably made of a durable material such as metals, but can also be made of other durable materials such as, but not limited to, plastic, polymeric, silicone, ceramic, bone, and composites of any such materials. Suitable polymers include polyether ether ketone (PEEK) and ultra-high molecular weight polyethylene (UHMWPE), as well as urethane dimethacrylate (DUDMA)/tri-ethylene glycol dimethacrylate (TEDGMA) blended resin. Certain embodiments of the invention may be comprised of a biocompatible, polymeric matrix reinforced with bioactive fillers, fibers, or both. Certain embodiments of the invention may be comprised of urethane dimethacrylate (DUDMA)/tri-ethylene glycol dimethacrylate (TEDGMA) blended resin and a plurality of fillers and fibers including bioactive fillers and E-glass fibers.

Durable materials may also consist of any number of pure metals, metal alloys, or both. Titanium and its alloys are generally preferred for certain embodiments of the invention due to their acceptable, and desirable, strength and biocompatibility. Suitable metals may comprise titanium, an alloy of titanium such as an aluminum and vanadium alloy of titanium (e.g., 6-4), a nickel alloy of titanium such as nitinol, a cobalt chromium alloy, surgical grade steel, stainless steel, or stainless steel alloy. In this manner, certain embodiments of the present interbody spinal implant may have improved structural integrity and may better resist fracture during implantation by impact. Interbody spinal implants, as now taught, may therefore be used as a distractor or trial implant during implantation.

The invention relates to an implant and to an associated instrument used to manipulate and place the implant in a patient. The invention also relates to a system including both of the implant and the instrument as components. Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the invention, allow for improved visualization of implant seating and fusion assessment. Interbody spinal implants, as now taught, may also facilitate osteointegration with the surrounding living bone.

Figure 3:
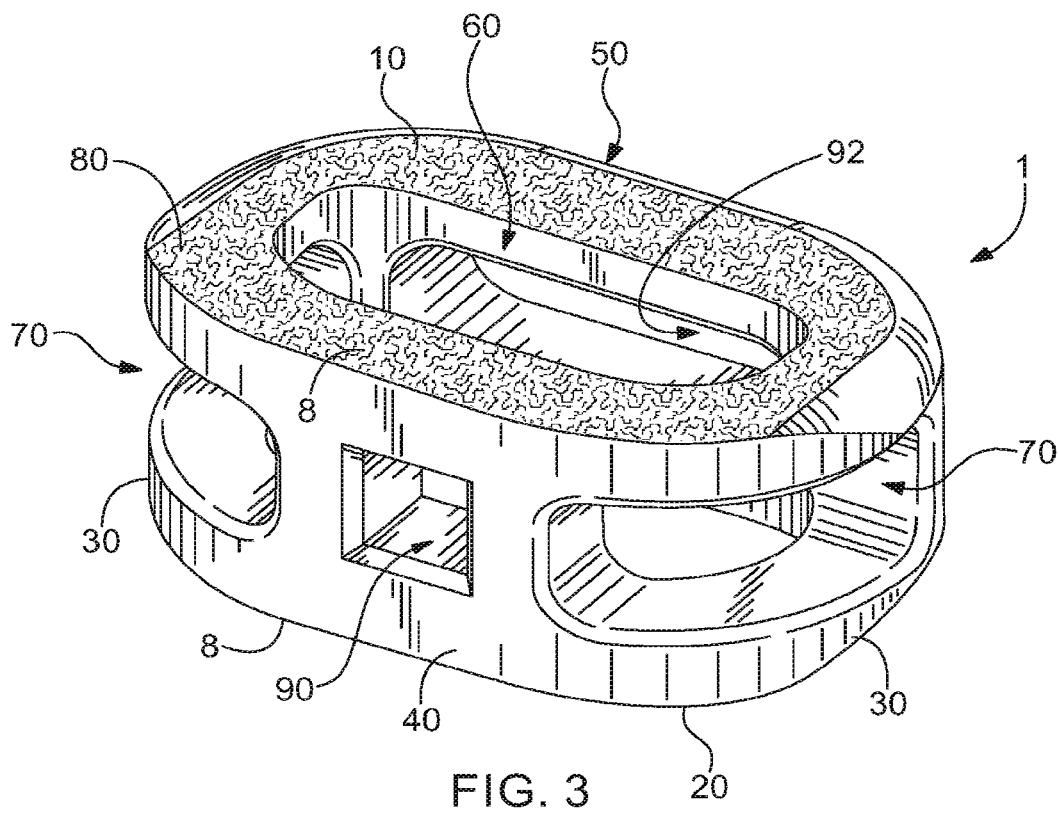
FIG. 3 shows a perspective view of an embodiment of the interbody spinal implant especially well adapted to be used in connection with an anterior lumbar interbody fusion (ALIF} surgical procedure.

FIG. 3 shows a perspective view of a first embodiment of the interbody spinal implant 1 especially well adapted for use in an ALIF procedure. The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. The roughened topography 80 is distinct, however, from the teeth provided on the surfaces of some conventional devices.

The implant 1 may include an anti-expulsion edge 8 at the junction between the top surface 10 and the anterior portion 40, at the junction between the bottom surface 20 and the anterior portion 40, or, as illustrated in FIG. 3, at both junctions. The anti-expulsion edge 8 helps to maintain the implant 1 in place, inhibiting migration and reducing the risk of undesired pull-out.

Figure 4:
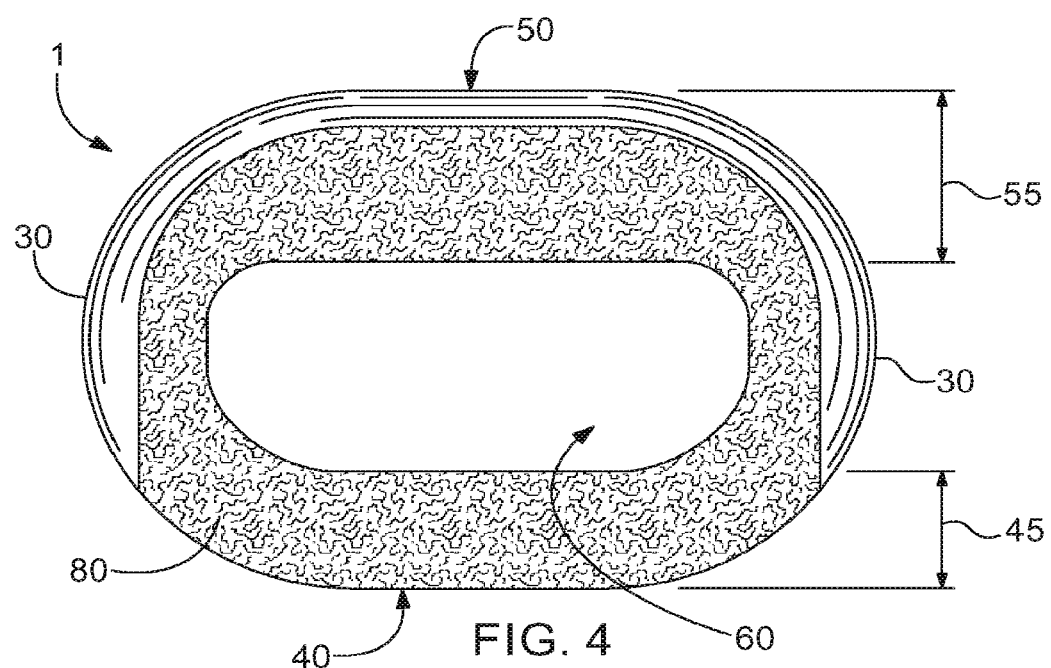
FIG. 4 shows a top view of the interbody spinal implant illustrated in FIG. 3.

In some aspects, the interbody spinal implant 1 is substantially hollow and has a generally oval-shaped transverse cross-sectional area with smooth, rounded, or both smooth and rounded lateral sides 30 and posterior-lateral corners. A substantially hollow implant 1 includes an implant 1 having at least about 33% of the interior volume of the implant 1 vacant. The implant 1 includes at least one vertical aperture 60 that extends the entire height of the implant body. As illustrated in the top view of FIG. 4, the vertical aperture 60 may further define a transverse rim 100 having a greater posterior portion thickness 55 than an anterior portion thickness 45.

In at least one embodiment, the opposing lateral sides 30 and the anterior portion 40 have an anterior portion thickness 45 of about 5 mm, while the posterior portion 50 has a posterior portion thickness 55 of about 7 mm. Thus, the posterior portion thickness 55 may allow for better stress sharing between the implant 1 and the adjacent vertebral endplates and helps to compensate for the weaker posterior endplate b one. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a posterior portion thickness 55 less than that of the opposing lateral sides 30 and the anterior portion 40. Some studies have challenged the characterization of the posterior endplate bone as weaker.

The implant 1 may also have a lordotic angle to facilitate alignment. The anterior portion 40 is preferably generally greater in height than the posterior portion 50. Therefore, the implant 1 may better compensate for the generally less supportive bone found in certain regions of the vertebral endplate.

The implant 1 may further include at least one transverse aperture 70. Like the vertical aperture 60, the size and shape of the transverse aperture 70 are carefully chosen (and predetermined) to achieve a preferable design tradeoff for the particular application envisioned for the implant 1. (By "predetermined" is meant determined beforehand, so that the predetermined characteristic must be determined, i.e., chosen or at least known, in advance of some event—in this case before the manufacture of the implant 1.) Specifically, the transverse aperture 70 should have minimal dimensions to maximize the strength and structural integrity of the implant 1. On the other hand, the transverse aperture 70 should have maximum dimensions to (a) improve the visibility of the implant 1 during surgical procedures to ensure proper implant placement and seating, and to improve post-operative assessment of implant fusion, and (b) to facilitate engagement between bone graft material and adjacent bone. The substantially hollow area defined by the implant 1 may be filled with bone graft materials to facilitate the formation of a solid fusion column within the spine of a patient.

As illustrated in FIG. 3, the implant 1 has an opening 90 in the anterior portion 40. The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement. A corresponding orifice 92 may be provided in the posterior portion 50. The opening 90 and orifice 92 facilitate both insertion of graft material into the interior of the implant 1 and improve visualization of the implant 1.

Figure 5:
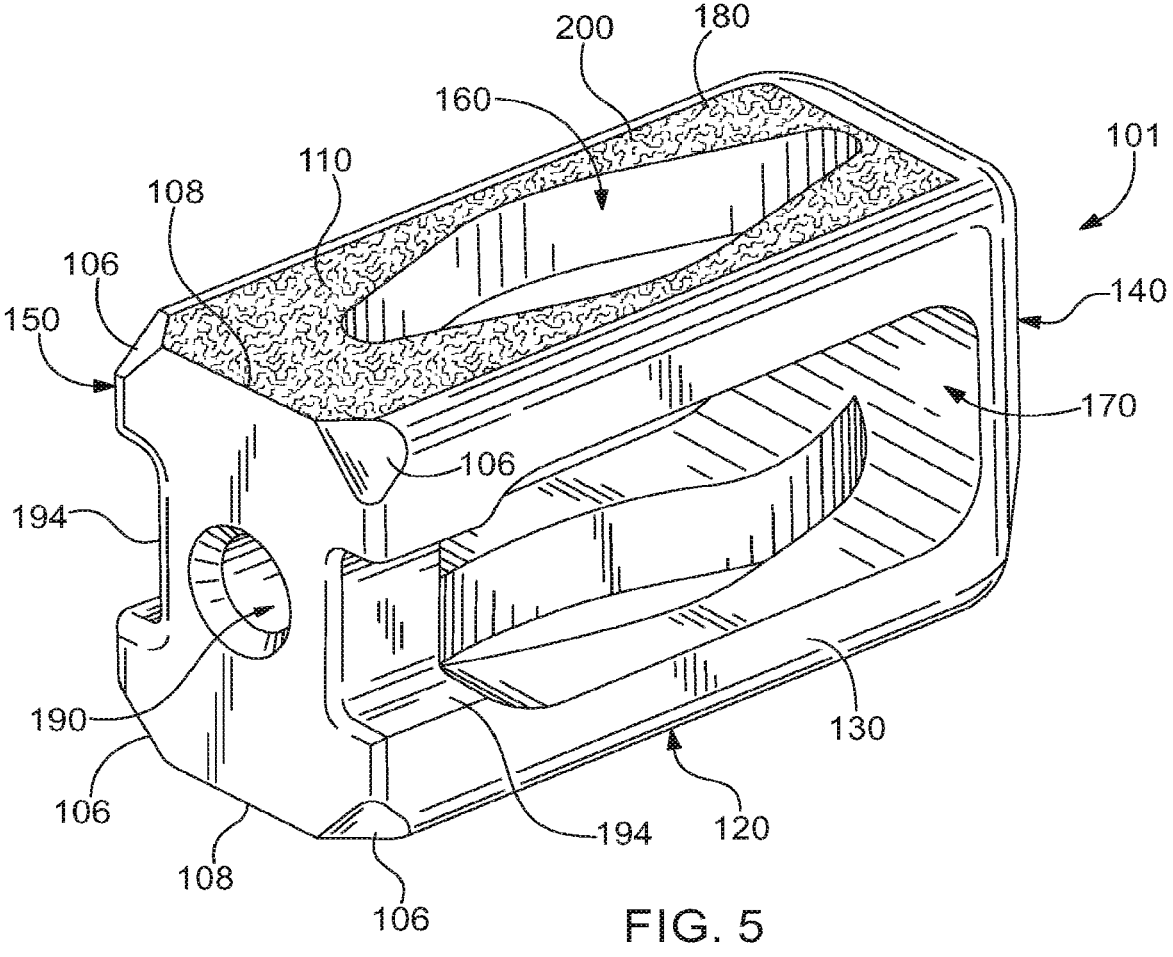
FIG. 5 shows a perspective view from the front of another embodiment of the interbody spinal implant especially well adapted to be used in connection with a posterior lumbar interbody fusion (PLIF} surgical procedure.
Figure 6:
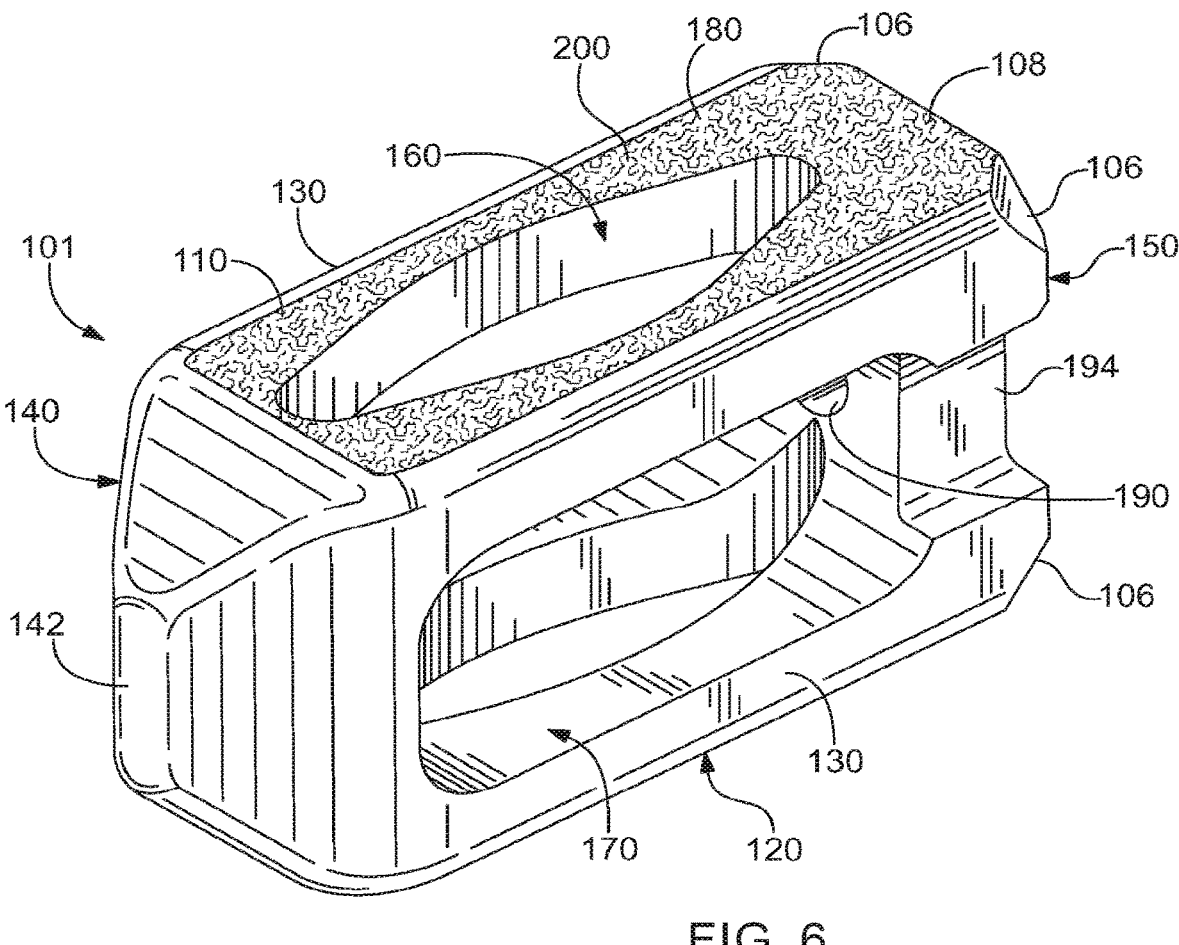
FIG. 6 shows a perspective view from the rear of the embodiment of the interbody spinal implant illustrated in FIG. 5.

As noted above, FIG. 3 shows a perspective view of one embodiment of the invention, the interbody spinal implant 1, which is especially well adapted for use in an ALIF procedure. Other embodiments of the invention are better suited for PLIF, TLIF, or cervical fusion procedures. Specifically, FIGS. 5 and 6 show perspective views of an embodiment of an interbody spinal implant 101 especially well adapted for use in a PLIF procedure. The interbody spinal implant 101 includes a body having a top surface 110, a bottom surface 120, opposing lateral sides 130, and opposing anterior 140 and posterior 150 portions. One or both of the top surface 110 and the bottom surface 120 has a roughened topography 180 for gripping adjacent bone and inhibiting migration of the implant 101.

Certain embodiments of the interbody spinal implant 101 are substantially hollow and have a generally rectangular shape with smooth, rounded, or both smooth and rounded lateral sides and anterior-lateral corners. As shown in FIG. 6, the anterior portion 140 may have a tapered nose 142 to facilitate insertion of the implant 101. To further facilitate insertion, the implant 101 has chamfers 106 at the corners of its posterior portion 150. The chamfers 106 prevent the implant 101 from catching upon insertion, risking potential damage such as severed nerves, while still permitting the implant 101 to have an anti-expulsion edge 108.

The implant 101 includes at least one vertical aperture 160 that extends the entire height of the implant body. The vertical aperture 160 further defines a transverse rim 200. The size and shape of the vertical aperture 160 are carefully chosen to achieve a preferable design tradeoff for the particular application envisioned for the implant 101. Specifically, the vertical aperture 160 seeks to maximize the surface area of the top surface 110 and the bottom surface 120 available proximate the anterior 140 and posterior 150 portions while maximizing both radiographic visualization and access to the bone graft material toward the center of the top 110 and bottom 120 surface s. Thus, the size and shape of the vertical aperture 160 are predetermined by the application in which the implant 101 will be used.

In the particular example shown in FIGS. 5 and 6, the width of the implant 101 between the two lateral sides 130 is approximately 9 mm. The shape of the vertical aperture 160 approximates, in cross section, that of an American football. The center of the vertical aperture 160, which defines the maximum width of the vertical aperture 160, is about 5 mm. Thus, the thickness of the transverse rim 200 on either side of the vertical aperture 160 adjacent the center of the vertical aperture 160 is about 2 mm. These dimensions permit ample engagement between the bone graft material contained within the implant 101 and bone.

The vertical aperture 160 tapers from its center to its ends along a longitudinal distance of about 7.75 mm (thus, the total length of the vertical aperture 160 is about 15.5 mm). This shape leaves intact much of the transverse rim 200 in the areas around the ends of the vertical aperture 160. These areas may allow for better stress sharing between the implant 101 and the adjacent vertebral endplate s. Thus, the transverse rim 200 has a generally large surface area and contacts the vertebral endplate.

As illustrated in FIG. 5, the implant 101 has an opening 190 in the posterior portion 150. The opening 190 has a number of functions. One function is to facilitate manipu- lation of the implant 101 by the caretaker. Thus, the care- taker may insert a surgical tool into the opening 190 and, through the engagement between the surgical tool and the opening 190, manipulate the implant 101. The opening 190 may be threaded to enhance the engagement.

The implant 101 may also have an Implant Holding Feature (IHF) 194 instead of or in addition to the opening 190. As illustrated in FIG. 5, the IHF 194 is located proximate the opening 190 in the posterior portion 150. In this particular example, the IHF 194 is a U-shaped notch. Like the opening 190, the IHF 194 has a number of functions, one of which is to facilitate manipulation of the implant 101 by the caretaker. Other functions of the opening 190 and the IHF 194 are to increase visibility of the implant 101 during surgical procedures and to enhance engagement between bone graft material and adjacent bone.

The implant 101 may further include at least one trans- verse aperture 170. Like the vertical aperture 160, the size and shape of the transverse aperture 170 are carefully chosen (and predetermined) to achieve a preferable design tradeoff for the particular application envisioned for the implant 101. Specifically, the transverse aperture 170 should have mini- mal dimensions to maximize the strength and structural integrity of the implant 101. On the other hand, the trans- verse aperture 170 should have maximum dimensions to (a) improve the visibility of the implant 101 during surgical procedures to ensure proper implant placement and seating, and to improve post-operative assessment of implant fusion, and (b) to facilitate engagement between bone graft material and adjacent bone. The substantially hollow area defined by the implant 101 may be filled with bone graft materials to facilitate the formation of a solid fusion column within the spine of a patient.

As shown in FIGS. 5 and 6, the transverse aperture 170 extends the entire transverse length of the implant body and nearly the entire height of the implant body. Thus, the size and shape of the transverse aperture 170 approach the maximum possible dimensions for the transverse aperture 170.

The section of the transverse aperture 170 proximate the IHF 194 is substantially rectangular in shape; the other section of the transverse aperture 170 has the shape of a curved arch. Other shapes and dimensions are suitable for the transverse aperture 170. In particular, all edges of the transverse aperture 170 may be rounded, smooth, or both.

The embodiment of the invention illustrated in FIGS. 5 and 6 is especially well suited for a PLIF surgical procedure. TLIF surgery is done through the posterior (rear) part of the spine and is essentially like an extended PLIF procedure. The TLIF procedure was developed in response to some of the technical problems encountered with a PLIF procedure. The main difference between the two spine fusion proce- dures is that the TLIF approach to the disc space is expanded by removing one entire facet joint; a PLIF procedure is usually done on both sides by only taking a portion of each of the paired facet joints.

By removing the entire facet joint, visualization into the disc space is improved and more disc material can be removed. Such removal should also provide for less nerve retraction. Because one entire facet is removed, the TLIF procedure is only done on one side: removing the facet joints on both sides of the spine would result in too much insta- bility. With increased visualization and room for dissection, one or both of a larger implant and more bone graft can be used in the TLIF procedure. Theoretically, these advantages can allow the spine surgeon to distract the disc space more and realign the spine better (re-establish the normal lumbar lordosis).

Although the TLIF procedure offers some improvements over a PLIF procedure, the anterior approach in most cases still provides the best visualization, most surface area for healing, and the best reduction of any of the approaches to the disc space. These advantages must be weighed, however, against the increased morbidity (e.g., unwanted aftereffects and postoperative discomfort) of a second incision. Probably the biggest determinate in how the disc space is approached is the comfort level that the spine surgeon has with an anterior approach for the spine fusion surgery. Not all spine surgeons are comfortable with operating around the great vessels (aorta and vena cava) or have access to a skilled vascular surgeon to help them with the approach. Therefore, choosing one of the posterior approaches for the spine fusion surgery is often a more practical solution.

Figure 7:
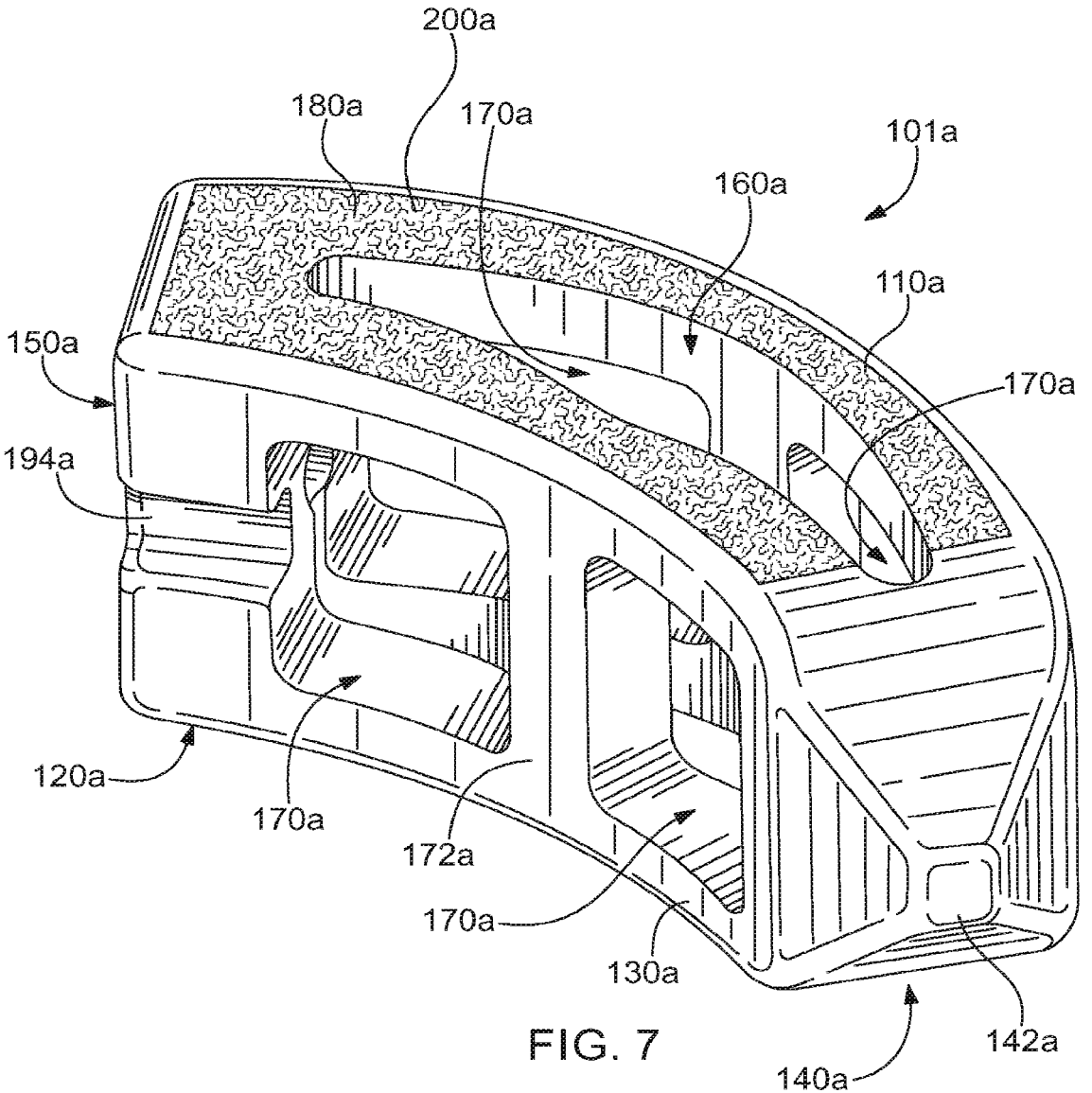
FIG. 7 shows a perspective view of another embodiment of the interbody spinal implant especially well adapted to be used in connection with a transforaminal lumbar interbody fusion (TLIF) surgical procedure.

The embodiment of the invention illustrated in FIG. 7 is especially well suited when the spine surgeon elects a TLIF procedure. Many of the features of the implant 101a illus- trated in FIG. 7 are the same as those of the implant 101 illustrated in FIGS. 5 and 6. Therefore, these features are given the same reference numbers, with the addition of the letter "a," as those described with respect to the implant 101. The interbody spinal implant 101a includes a body having a top surface 110a, a bottom surface 120a, opposing lateral sides 130a, and opposing anterior 140a and posterior 150a portions. The anterior portion 140a may have a tapered nose 142a to facilitate insertion of the implant 101a. One or both of the top surface 110a and the bottom surface 120a has a roughened topography 180a for gripping adjacent bone and inhibiting migration of the implant 101a. The implant 101a may also have an Implant Holding Feature (IHF) 194a.

There are several differences, however, between the two embodiments (e.g., implant 101 and implant 101a). For example, unlike the substantially rectangular shape of the implant 101, the implant 101a has a curved shape. Further, the chamfers 106 and anti-expulsion edge 108 of the implant 101 are replaced by curves or rounded edges for the implant 101a. Still further, the TLIF procedure often permits use of a larger implant 101a which, in turn, may affect the size and shape of the predetermined vertical aperture 160a.

The substantially constant 9 mm width of the transverse rim 200 of the implant 101 is replaced with a larger, curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 200) allows the shape of the vertical aperture 160a to change, in cross section, from approximating a football to approximating a boomerang. Maintaining the thickness of the transverse rim 200a on either side of the vertical aperture 160a adjacent the center of the vertical aperture 160a at about 2 mm, similar to the dimensions of the implant 101, the center of the vertical aperture 160a, which defines the maximum width of the vertical aperture 160a, is increased (from 5 mm for the implant 101) to about 7 mm.

The implant 101a may also have a lordotic angle to facilitate alignment. The lateral side 130a depicted at the top of the implant 101a is preferably generally greater in height than the opposing lateral side 130a. Therefore, the implant 101a may better compensate for the generally less supportive bone found in certain regions of the vertebral endplate.

As shown in FIG. 7, the transverse aperture 170a extends the entire transverse length of the implant body and nearly the entire height of the implant body. FIG. 7 also highlights an alternative transverse aperture 170a, where the transverse aperture 170a is broken into two, separate sections by an intermediate wall 172a. Thus, the dimensions of the transverse aperture 170a shown in FIG. 7 are much smaller than those for a single transverse aperture 170a. The two sections of the alternative transverse aperture 170a are each illustrated as substantially rectangular in shape and extending nearly the entire height of the implant body; other sizes and shapes are possible for one or both sections of the alternative transverse aperture 170a.

The intermediate wall 172a may be made of the same material as the remainder of the implant 101a (e.g., metal), or it may be made of another material (e.g., PEEK) to form the composite implant 101a. It is also possible to extend the intermediate wall 172a, whether made of metal, PEEK, ultra-high molecular weight polyethylene (UHMWPE), or another material, to eliminate entirely the transverse aperture 170a. Given the reinforcement function of the intermediate wall 172a, the length of the vertical aperture 160a can be extended (as shown in FIG. 7) beyond the top surface 110a and into the anterior portion 140a of the implant 101a.

The embodiments of the invention described above are best suited for one or more of the ALIF, PLIF, and TLIF surgical procedures. Another embodiment of the invention is better suited for cervical fusion procedures. This embodiment is illustrated in FIGS. 8A and 8B as the interbody spinal implant 201.

Because there is not a lot of disc material between the vertebral bodies in the cervical spine, the discs are usually not very large. The space available for the nerves is also not that great, however, which means that even a small cervical disc herniation may impinge on the nerve and cause significant pain. There is also less mechanical load on the discs in the cervical spine as opposed to the load that exists lower in the spine. Among others, these differences have ramifications for the design of the implant 201.

The implant 201 is generally smaller in size than the other implant embodiments. In addition, the lower mechanical load requirements imposed by the cervical application typically render a composite implant unnecessary. Therefore, the implant 201 is generally made entirely of metal (e.g., titanium) and devoid of other materials (e.g., PEEK).

Figure 8A:
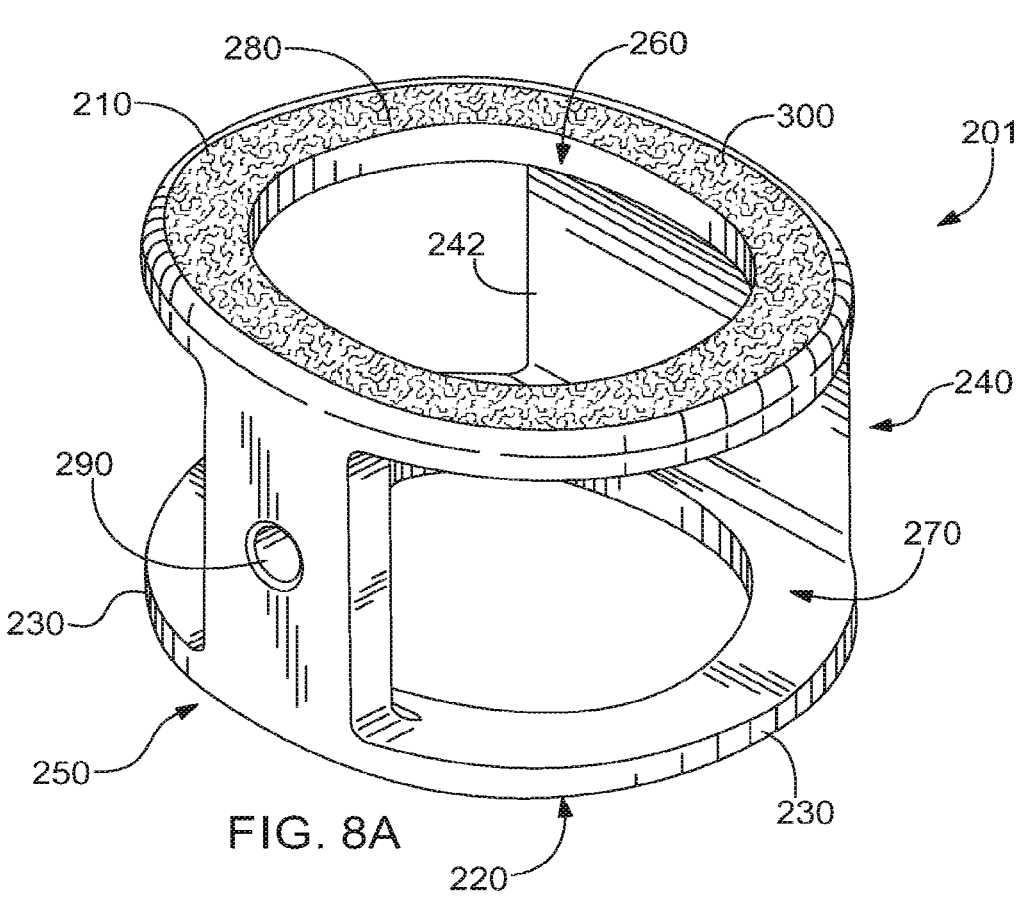
FIG. 8A shows a perspective view of another embodiment of the interbody spinal implant having a generally oval shape and being especially well adapted to be used in connection with a cervical spine surgical procedure.
Figure 8B:
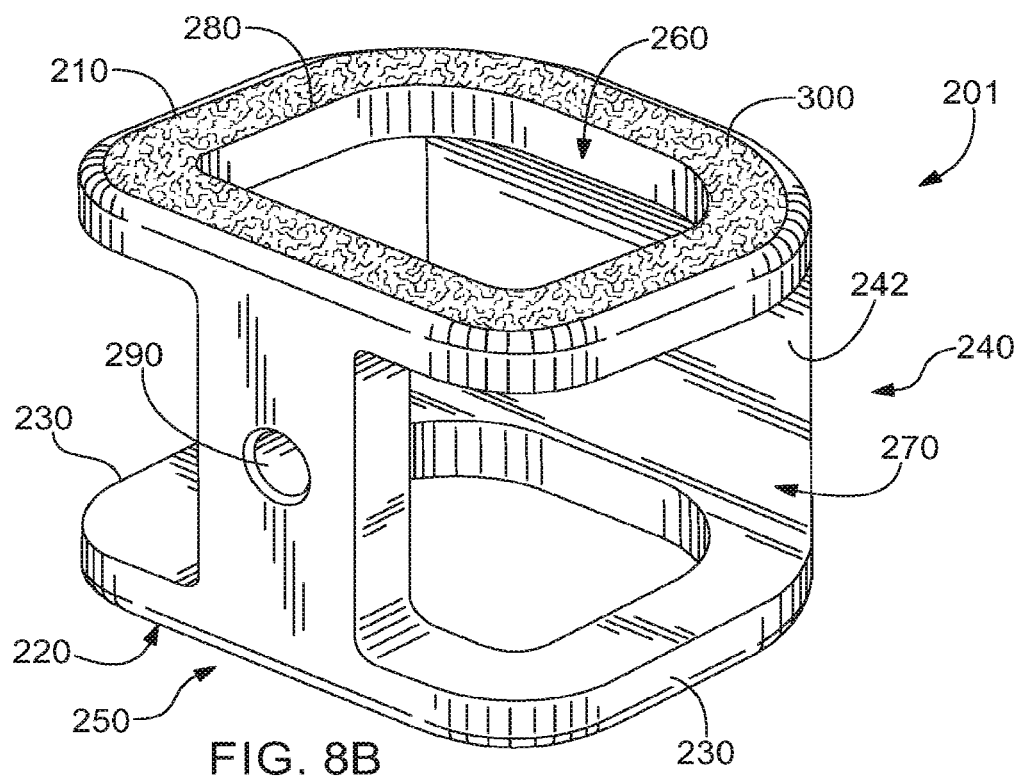
FIG. 8B shows a perspective view of a cervical implant having a generally box shape.

With specific reference to FIG. 8A and FIG. 8B, the implant 201 includes a body having a top surface 210, a bottom surface 220, opposing lateral sides 230, and opposing anterior 240 and posterior 250 portions. One or both of the top surface 210 and the bottom surface 220 has a roughened topography 280 for gripping adjacent bone and inhibiting migration of the implant 201. The implant 201 is substantially hollow and has a generally oval shape with smooth, rounded, or both smooth and rounded edges.

The implant 201 includes at least one vertical aperture 260 that extends the entire height of the implant body. The vertical aperture 260 further defines a transverse rim 300. The size and shape of the vertical aperture 260 are carefully chosen to achieve a preferable design tradeoff for the particular application envisioned for the implant 201. Specifically, the vertical aperture 260 seeks to maximize the surface area of the top surface 210 and the bottom surface 220, to allow for better stress sharing between the implant 201 and the adjacent vertebral endplates, while maximizing access to the bone graft material provided within the implant 201. Thus, the size and shape of the vertical aperture 260 are predetermined by the application.

As illustrated in FIG. 8A, the implant 201 has an opening 290 in the posterior portion 250. The opening 290 has a number of functions. One function is to facilitate manipulation of the implant 201 by the caretaker. Thus, the caretaker may insert a surgical tool into the opening 290 and, through the engagement between the surgical tool and the opening 290, manipulate the implant 201. The opening 290 may be threaded to enhance the engagement.

The implant 201 may further include at least one transverse aperture 270. Like the vertical aperture 260, the size and shape of the transverse aperture 270 are carefully chosen (and predetermined) to achieve a preferable design tradeoff for the particular application envisioned for the implant 201. For example, as shown in FIG. 8A, the transverse aperture 270 may extend the entire transverse length of the implant body and nearly the entire height of the implant body. Thus, the size and shape of the transverse aperture 270 approach the maximum possible dimensions for the transverse aperture 270.

As illustrated in FIG. 8A, the implant 201 may be provided with a solid rear wall 242. The rear wall 242 extends the entire width of the implant body and nearly the entire height of the implant body. Thus, the rear wall 242 essentially closes the anterior portion 240 of the implant 201. The rear wall 242 may offer one or more of several advantages, including reinforcement of the implant 201 and improved bone graft containment. In the cervical application, it may be important to prevent bone graft material from entering the spinal canal.

Alternative shapes for the implant 201 are possible. As illustrated in FIG. 8B, for example, the implant 201 may have a generally box shape which gives the implant 201 increased cortical bone c overage. Like the implant 201 shown in FIG. 8A, the implant 201 shown in FIG. 8B has a curved transverse rim 300 in the area of the anterior portion 240. The shape of the posterior portion 250 of the implant 201 is substantially flat, however, and the shape of the transverse rim 300 in the area of the posterior portion 250 is substantially square. Thus, the posterior portion 250 provides a face that can receive impact from a tool, such as a surgical hammer, to force the implant 201 into position.

The implant 201 may also have a lordotic angle to facilitate alignment. As illustrated in FIGS. 8A and 8B, the anterior portion 240 is preferably generally greater in height than the posterior portion 250. Therefore, the implant 201 may better compensate for the generally less supportive bone found in certain regions of the vertebral endplate. As an example, four degrees of lordosis may be built into the implant 201 to help restore balance to the spine.

Certain embodiments of the implant 1, 101, 101a, and 201 are generally shaped (i.e., made wide) to maximize contact with the apophyseal rim of the vertebral endplates. They are designed to be impacted between the endplates, with fixation to the endplates created by an interference fit and annular tension. Thus, the implants 1, 101, 101*a*, and 201 are shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis {or more) may be built into the implants 1, 101, 101*a*, and 201 to help restore cervical balance.

When endplate-sparing spinal implant 1, 101, 101*a*, and 201 seats in the disc space against the apophyseal rim, it should still allow for deflection of the endplates like a diaphragm. This means that, regardless of the stiffness of the spinal implant 1, 101, 101*a*, and 201, the bone graft material inside the spinal implant 1, 101, 101*a*, and 201 receives load, leading to healthy fusion. The vertical load in the human spine is transferred though the peripheral cortex of the vertebral bodies. By implanting an apophyseal-supporting inter-body implant 1, 101, 101*a*, and 201, the natural bio-mechanics may be better preserved than for conventional devices.

Figure 15:
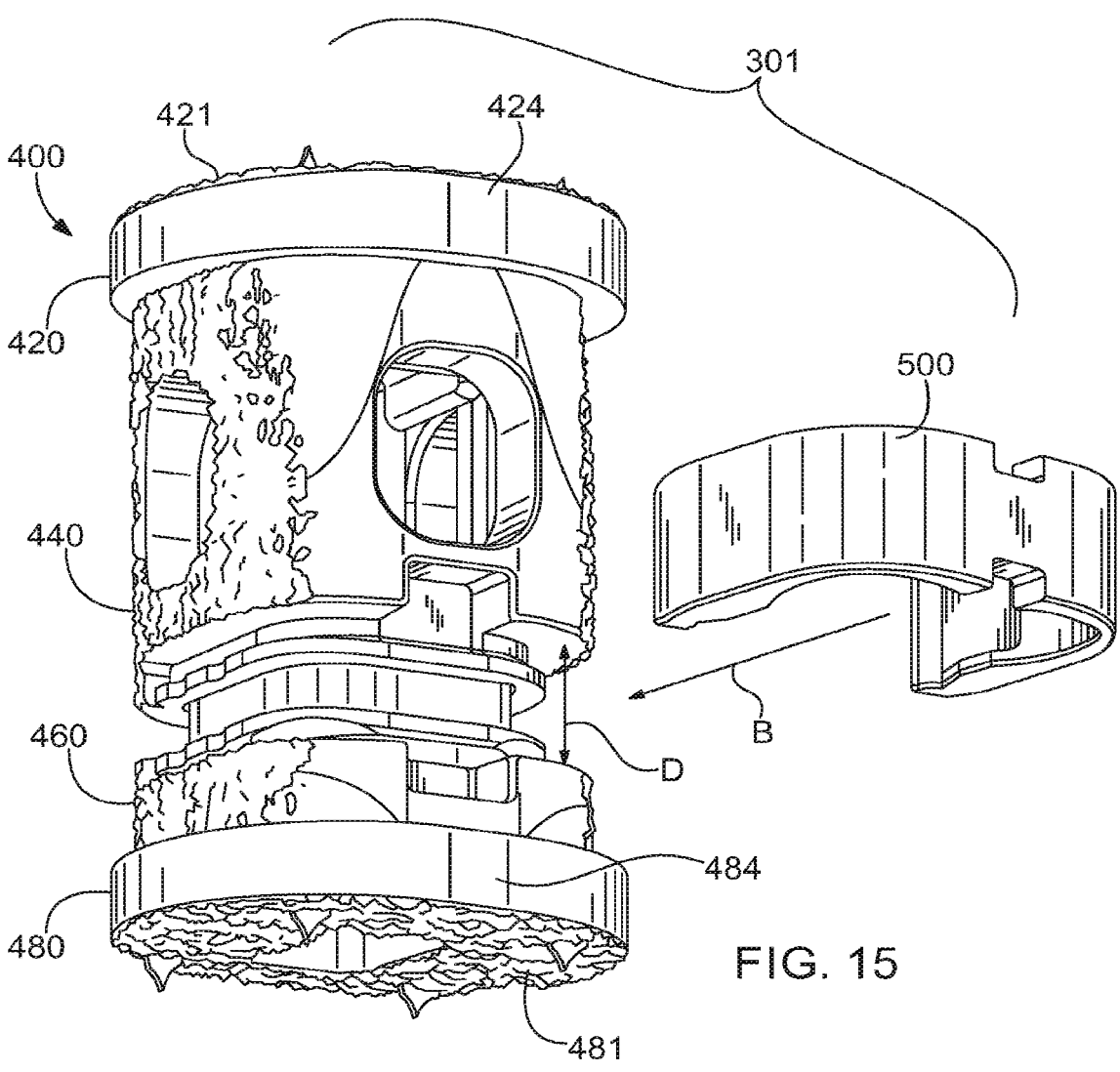
FIG. 15 illustrates the shim shown in FIGS. 14A and 14B aligned and poised for engagement with the cage shown in FIG. 13 to complete assembly of an embodiment of the interbody spinal implant.
Figure 16:
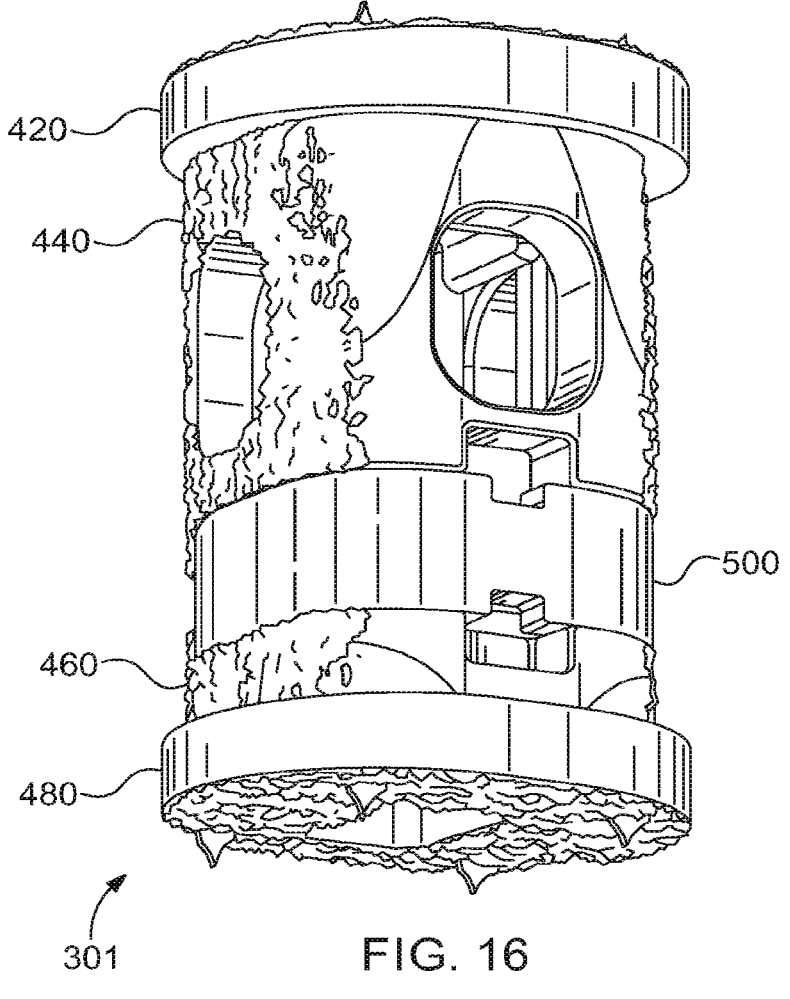
FIG. 16 illustrates the cage shown in FIG. 13 as fully engaged with the shim shown in FIGS. 14A and 14B, thereby completing assembly of an embodiment of the interbody spinal implant.

In another embodiment of the present invention, an inter-body spinal implant 301 is a composite modular device that combines the benefits of two, separate components: a modular adjustable corpectomy cage 400 and a shim 500. One or more of the features illustrated and described above for the embodiments of the implant 1, 101, 101*a*, and 201 can be incorporated into the implant 301. The composite structure of implant 301 advantageously permits the engineering designer of the implant 301 to balance the mechanical characteristics of the overall implant 301. Thus, the implant 301 can achieve the best balance, for example, of strength, resistance to subsidence, and stress transfer to bone graft. Moreover, the implant 301 can be inserted with minimal surgical modification. This combination of size and minimal surgical modification is advantageous. Like the embodiment of the implant 201 illustrated in FIGS. 8A and 8B, the embodiment of the implant 301 illustrated in FIGS. 15 and 16 is especially well suited for cervical fusion procedures.

Figure 9:
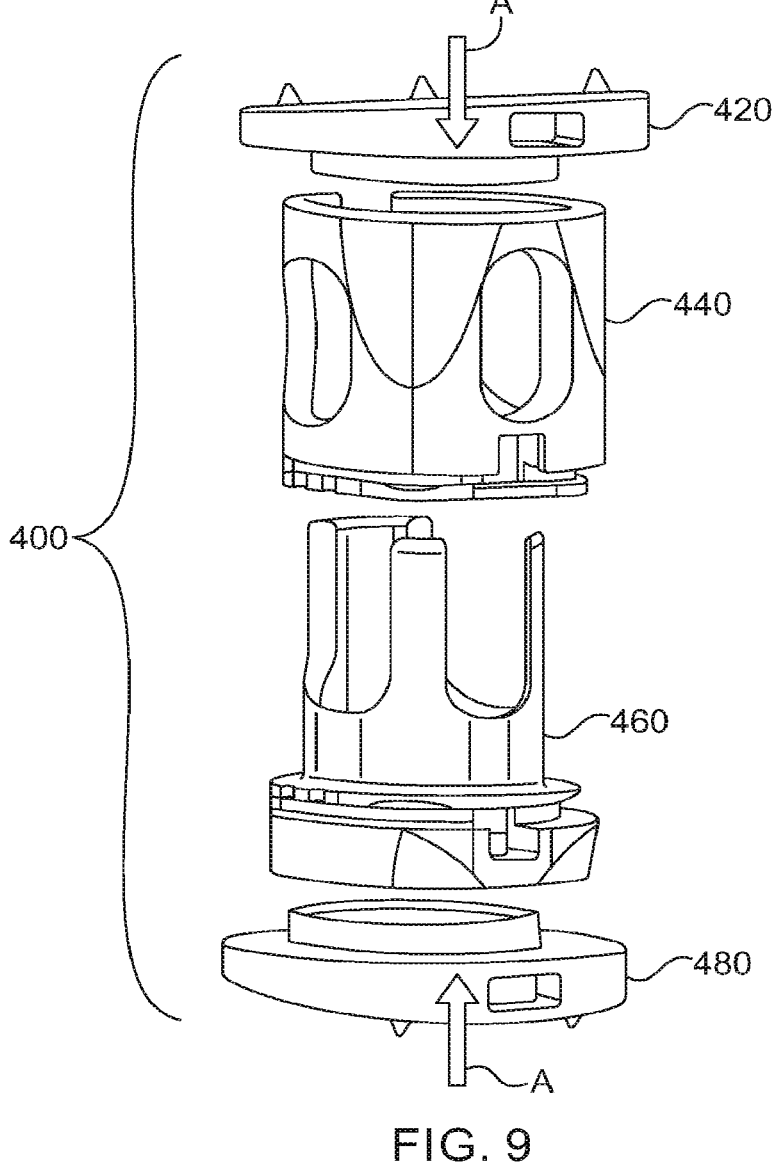
FIG. 9 shows a perspective view of one component of another embodiment of the interbody spinal implant, a modular adjustable corpectomy cage, especially well adapted to be used in connection with a cervical spine surgical procedure and illustrating the four modules of the cage in a disassembled (separated) state according to the invention.

FIG. 9 shows a perspective view of one component of the interbody spinal implant 301, the modular adjustable corpectomy cage 400, illustrating the four modules of the cage 400 in a disassembled {separated) state. The cage 400 includes a first {top) endplate 420, a body 440, a column 460, and a second (bottom) endplate 480. The cage 400 is assembled by moving the four modules towards each other in the direction of the arrows "A" in FIG. 9. When the cage 400 is fully assembled and the shim 500 is applied, the implant 301 appears as illustrated in FIG. 16. Each of the four modules that combine to form the cage 400 is discussed in turn.

Figure 10:
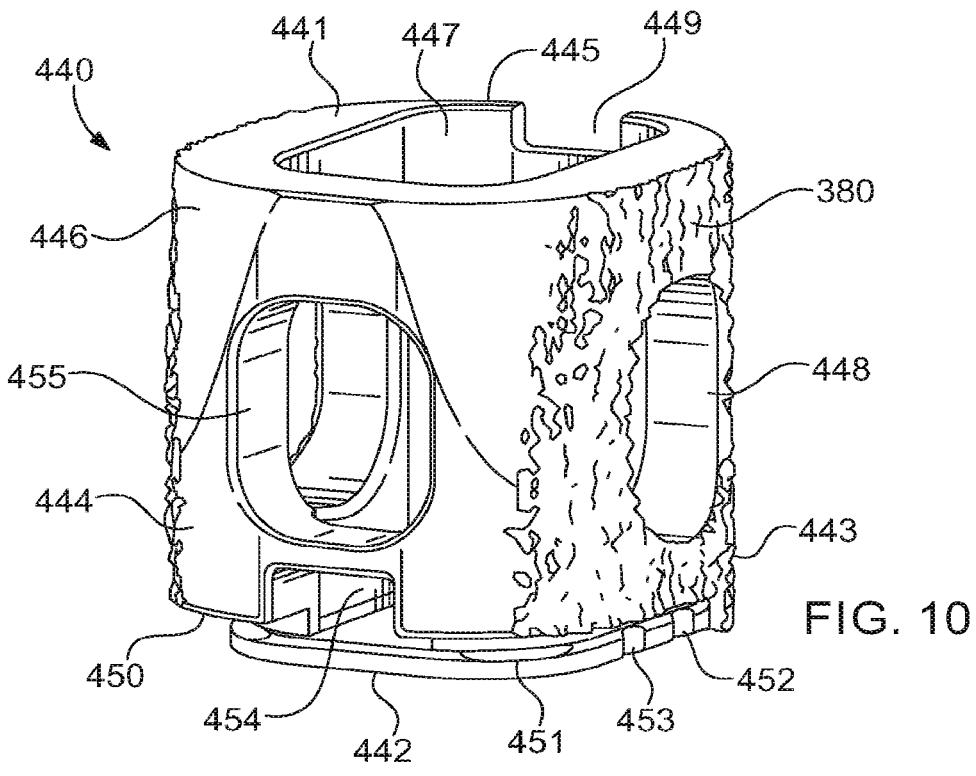
FIG. 10 illustrates one module of the cage shown in FIG. 9, namely the body of the cage.

FIG. 10 illustrates the body 440 of the cage 400. The body 440 has a top surface 441, a bottom surface 442, opposing lateral sides 443, and opposing anterior 444 and posterior 445 portions. At least the lateral sides 443 have a roughened topography 380 for gripping adjacent bone and inhibiting migration of the implant 301. The body 440 includes a transition portion 446 that gradually alters the shape of the body 440 from a generally square cross section in the middle and lower portions of the body 440, which is advantageous in resisting torque and accepting the shim 500, to a generally oval top surface 441 that matches the shape of the first endplate 420.

The body 440 includes at least one vertical aperture 447 that extends the entire height of the body 440. The body 440 also includes at least one transverse aperture 448 that extends the entire transverse length of the body 440 and a substantial portion of the height of the body 440. The posterior portion 445 has a key slot 449 that orients the first endplate 420 with respect to the body 440, enabling the user to place first endplate 420 on the body 440 easily.

The anterior portion 444 of the body 440 has a chamfer 450 located proximate the bottom surface 442. The chamfer 450 facilitates insertion of the shim 500 and placement of the shim 500 into engagement with the body 440. The body 440 also has a track 451 that extends below the chamfer 450 and forms the bottom surface 442. The track 451 guides the shim 500 into its final position, engaging the body 440. The track 451 includes a final detent recess 452 for seating the shim 500 under the chamfer 450 and in the track 451. The track 451 also includes a backup detent recess 453 to retain the shim 500 should the shim 500 become dislodged from the final detent recess 452.

The anterior portion 444 further has a tool holding feature 454 adapted to engage a tool 600 (see below) to facilitate insertion of the cage 400. The anterior portion 444 still further has an anterior window 455 that, among other functions, facilitates packing of graft material inside the body 440. The anterior window 455 and the transverse aperture 448 also function to allow the caretaker to assess fusion of the implant 301 after the implant 301 has been placed in the patient.

Figure 11:
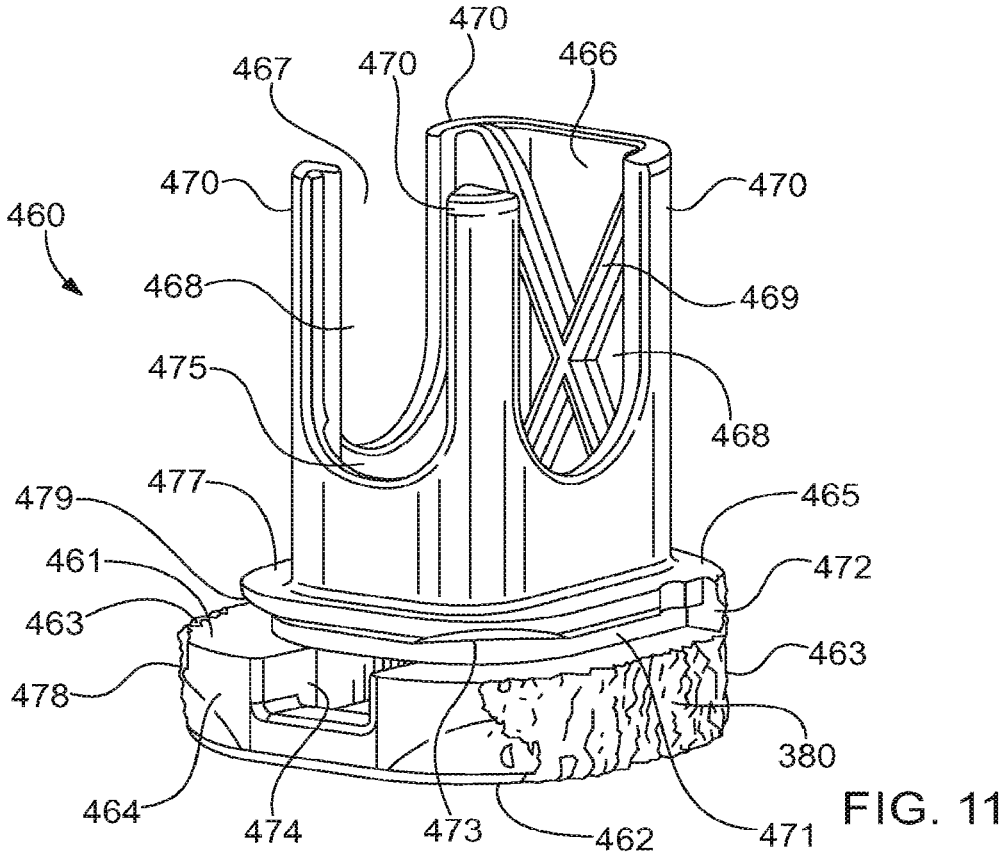
FIG. 11 illustrates a second module of the cage shown in FIG. 9, namely the column of the cage.
Figure 13:
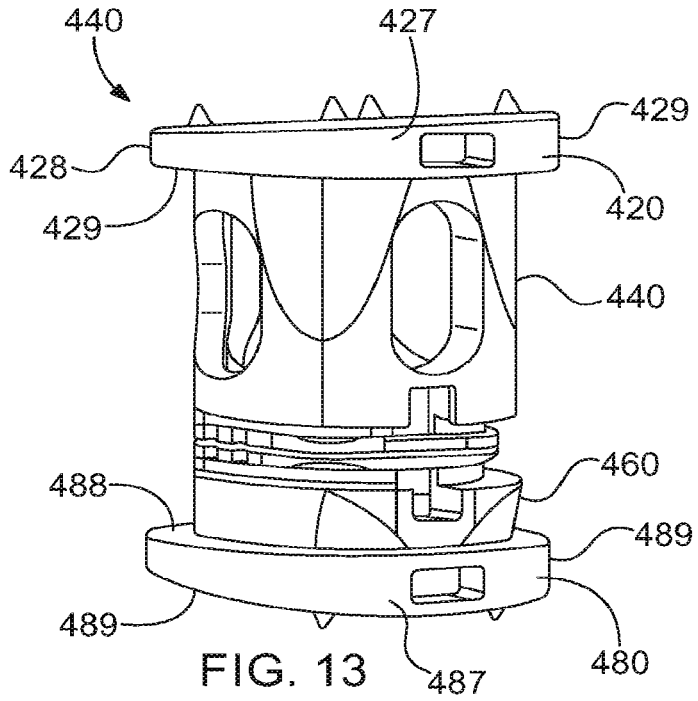
FIG. 13 illustrates the cage with its four modular components (the body, the column, the first endplate, and the second endplate) assembled together or combined to form the cage.

FIG. 11 illustrates the column 460 of the cage 400. The column 460 has a base 478 with a top surface 461, a bottom surface 462, opposing lateral sides 463, and opposing anterior 464 and posterior 465 portions. At least the lateral sides 463 have a roughened topography 380 for gripping adjacent bone and inhibiting migration of the implant 301. The anterior portion 464 further has a tool holding feature 474 adapted to engage the tool 600 to facilitate insertion of the cage 400. The tool holding feature 474 of the column 460 is aligned with the tool holding feature 454 of the body 440 when the column 460 and the body 440 are assembled together and engaged (as shown in FIG. 13).

The column 460 of the cage 400 also has a flange 477 extending around the column 460 above the base 478. The flange 477 defines an undercut 479 and a lead-in chamfer 473 that each facilitate insertion of the shim 500 and placement of the shim 500 into engagement with the column 460. The column 460 also has a track 471 that extends below the undercut 479 and between the flange 477 and the top surface 461 of the base 478. The track 471 guides the shim 500 into its final position, engaging the column 460. The track 471 includes a stop 472 for seating the shim 500 in the track 471 and preventing the flat distal faces 514,516 of the shim 500 (see FIG. 14A and the description below) from contacting anatomical structures—thereby enhancing safety.

Extending upward from the flange 477 of the column 460 are a plurality of legs 470. Although an alternative number of legs 470 would be suitable, four legs 470 are illustrated in FIG. 11. The legs 470 define an anterior window 475 that is aligned with the anterior window 455 of the body 440 when the column 460 and the body 440 are assembled together and engaged. Among other functions, when aligned, the anterior window 475 and the anterior window 454 facilitate packing of graft material inside the column 460.

The legs 470 further define at least one transverse aperture 468 that extends the entire transverse length of the column 460 and a substantial portion of the height of the column 460. The transverse aperture 468 of the column 460 is aligned with the transverse aperture 448 of the body 440 when the column 460 and the body 440 are assembled together and engaged. Among other functions, when the column 460 and the body 440 are engaged, (i) the anterior window 475 and the anterior window 455 and (ii) the transverse aperture 468 and the transverse aperture 448 allow the caretaker to assess fusion of the implant 301 after the implant 301 has been placed in the patient.

The legs 470 still further define a vertical aperture 467 that is aligned with the vertical aperture 447 of the body 440 when the column 460 and the body 440 are assembled together and engaged. The vertical aperture 467 extends the entire height of the legs 470 and substantially the entire height of the column 460. The size and shape of the vertical aperture 467 are predetermined by the application in which the implant 301 will be used.

As illustrated in FIG. 11, the column 460 has a solid rear wall 466. The rear wall 466 extends the entire width of the column 460 and nearly the entire height of the column 460. Thus, the rear wall 466 essentially closes the posterior portion 465 of the column 460. The rear wall 466 may offer one or more of several advantages, including reinforcement of the column 460 and improved bone graft containment. In the cervical application, it may be important to prevent bone graft material from entering the spinal canal. The rear wall 466 may itself be reinforced structurally by ribs 469, shown in FIG. 11 as a pair of crossing ribs 469 forming an "x" shape.

Figure 12:
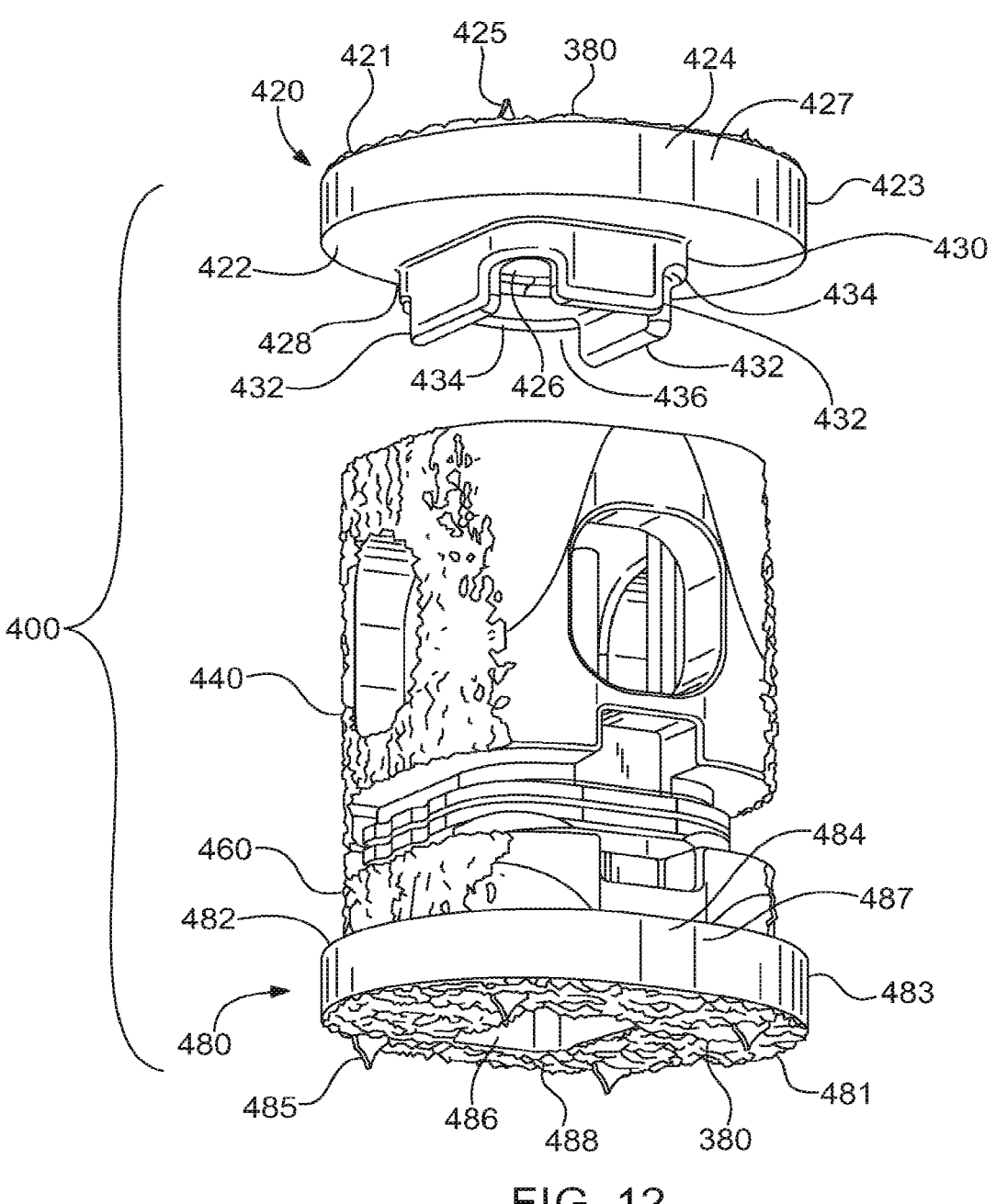
FIG. 12 illustrates the third and fourth modules of the cage shown in FIG. 9, namely the first (top) endplate and the second (bottom) endplate, with the body and the column (shown in FIGS. 10 and 11, respectively) assembled together and engaged fully, the second endplate assembled together and engaged with the column, and the first endplate unassembled, not yet engaged with the body, and, therefore, highlighted.

FIG. 12 illustrates the column 460 and the body 440 assembled together and engaged fully. When those two modular components of the cage 400 are engaged fully, the cage 400 has its minimum height. Assembly of the body 440 onto the column 460 is completed by sliding the body 440 over the legs 470 of the column 460 so that, as shown in FIG. 12, the legs 470 are contained at least partially (and possibly entirely, as shown) within the body 440. In this position, the vertical apertures 447, 467; the transverse apertures 448, 468; the tracks 451, 471; the tool holding features 454, 474; and the anterior windows 455, 475 of the body 440 and the column 460 all align. Given how the column 460 and the body 440 are assembled together, the column 460 might be called the male, inner, or contained component while the body 440 might be called the female, outer, or surrounding component, respectively.

The height of the cage 400 can be adjusted to create multiple height combinations by separating the body 440 from the column 460. From the position of the body 440 and the column 460 shown in FIG. 12, i.e., the minimum height for the cage 400, the body 440 can slide upward and away from the column 460 under the force of an expanding tool (which engages the tool holding features 454, 474, as will be discussed in more detail below) to achieve any number of expanded positions. The greater the separation between the body 440 and the column 460, the greater the height of the cage 400. Once the body 440 and the column 460 are in the position that defines the height desired for a particular application, an appropriately sized shim 500 is selected, inserted along the tracks 451, 471, and snapped into position affixing the body 440 and the column 460 in the desired position. As will be discussed in more detail below, the tool 600 can be used to facilitate insertion of the shim 500 in situ.

FIG. 12 also illustrates the first (top) endplate 420 and the second (bottom) endplate 480 of the cage 400. Like the body 440 and the column 460, the first endplate 420 and the second endplate 480 are modular components. When assembled together, the body 440, the column 460, the first endplate 420, and the second endplate 480 combine to form the cage 400—as illustrated in FIG. 13.

The term "endplate" as used in this document is broadly intended to include not only structures that have a flat or substantially flat surface but also, for example, members that are curved or sloped or have regular or irregular formations, and that may or may not have openings extending through them. Although they might differ in structure, especially if a particular application requires a lordotic angle to facilitate alignment, the first endplate 420 and the second endplate 480 typically have the same structure. Thus, when assembled to form the cage 400, the first endplate 420 and the second endplate 480 are typically mirror images of one another. Therefore, a description of the first endplate 420 often (although not necessarily) suffices to describe the second endplate 480.

The endplate 420, 480 has a top surface 421, 481; a bottom surface 422, 482; an anterior portion 427, 487; a posterior portion 428, 488; and opposing lateral sides 429, 489. A neck 423, 483 is disposed between the top surface 421, 481 and the bottom surface 422, 482. The top surface 421, 481 may be constructed much like the top surface 10, 110, 110*a*, 210 depicted above for the implant 1, 101, 101*a*, 201 of other embodiments. As shown in FIGS. 12, 15, and 16 for the implant 301, however, the top surface 421, 481 has a substantially oval shape; a vertical aperture 426, 486; a roughened topography 380 for gripping adjacent bone and inhibiting migration of the implant 301; and, optionally, a plurality of retention barbs 425, 485.

The neck 423, 483 follows the shape of the top surface 421, 481. Thus, as shown in FIGS. 12, 15, and 16, the neck 423, 483 has a substantially oval shape. That oval shape is interrupted, however, by a relatively narrow straight, flat portion 424, 484. Typically, although not necessarily, the flat portion 424, 484 is located in the anterior portion 427, 487 of the endplate 420, 480. The flat portion 424, 484 is designed to match the anatomy of the patient and to provide a flat surface that most easily and effectively receives the force of impact delivered by a hammer or other instrument. The flat portion 424, 484 can also help to stabilize an instrument such as the tool 600 as the instrument engages the cage 400.

The vertical aperture 426, 486 extends through the top surface 421, 481; traverses the entire length of the endplate 420, 480; and extends through the bottom surface 422, 482. At the bottom surface 422, 482, the vertical aperture 426, 486 mates with, and matches in size and shape, both the vertical aperture 447 of the body 440 and the vertical aperture 467 of the column 460. Thus, a single vertical aperture extends through the entire length of the cage 400 and, therefore, of the implant 301 (because the shim 500 does not impact the vertical aperture).

As shown in FIG. 12, projecting away from the top surface 421, 481 of the end plate 420, 480 are a plurality of retention barbs 425, 485. The retention barbs 425, 485 function to frictionally engage with adjacent bone so as to enhance fixation and resist implant migration or movement of the implant 301 relative to the bone. In alternative embodiments, an artisan would appreciate that any number of one or more retention barbs 425, 485 can be mounted on the top surface 421, 481 of the endplate 420, 480 and that the retention barbs 425, 485 can have any desired configuration so as to effectively engage with bone. For example, in alternative embodiments the retention barbs 425, 485 can comprise discrete teeth or aligned racks of teeth. An artisan would also appreciate that the retention barbs 425, 485 can be oriented at a common or at different angles so as to more effectively prevent movement in a specific direction.

Projecting away from the bottom surface 422, 482 of the endplate 420, 480 is a seat 430 (490 not shown). The seat 430 (490) has a plurality of uprights 432 (492 not shown) separated by cutouts 434 (494 not shown). As illustrated in FIG. 12, three uprights 432 (492) and two cutouts 434 (494) are suitable. Different numbers of uprights 432, 492 and cutouts 434, 494 are possible, however, depending upon the application. Also provided in the seat 430, 490 is a void 436 (496 not shown).

The seat 430 (490) of the endplate 420, 480 fits inside, and engages via friction, the body 440 and the column 460. More specifically, the seat 430 secures the endplate 420 to the body 440 via a friction fit and the seat (490) secures the endplate 480 to the column 460 via a friction fit. In that manner, the modular endplates 420, 480 couple with the body 440 and the column 460 to form the cage 400. The cutouts 434 (494) of the seat 430 (490) allow for maximum engagement among the endplate 420, 480; the body 440; and the column 460 while avoiding interference between the seat 430 (490) and the legs 470 of the column 460 (and any other structure, for that matter). Similarly, the void 436 (496) of the seat 430 (490) allows for maximum engagement among the endplate 420, 480; the body 440; and the column 460 while avoiding interference between the seat 430 (490) and rear wall 466 of the column 460 (and any other structure, for that matter).

FIG. 13 illustrates the cage 400 with its four modular components (the first endplate 420, the body 440, the column 460, and the second endplate 480) assembled or engaged. The cage 400 and, therefore, the implant 301 may have a lordotic angle to facilitate alignment of the implant 301 with the anatomy of a patient. One or both of the lateral sides 429, 489 depicted at the right of the cage 400 in FIG. 13 may be generally greater in height than the opposing lateral sides 429, 489. One or both of the anterior portions 427, 487 depicted at the front of the cage 400 in FIG. 13 may be generally greater in height than the posterior portions 428, 488. Therefore, the implant 301 may better compensate for the generally less supportive bone found in certain regions of the vertebral endplate.

Figure 14A:
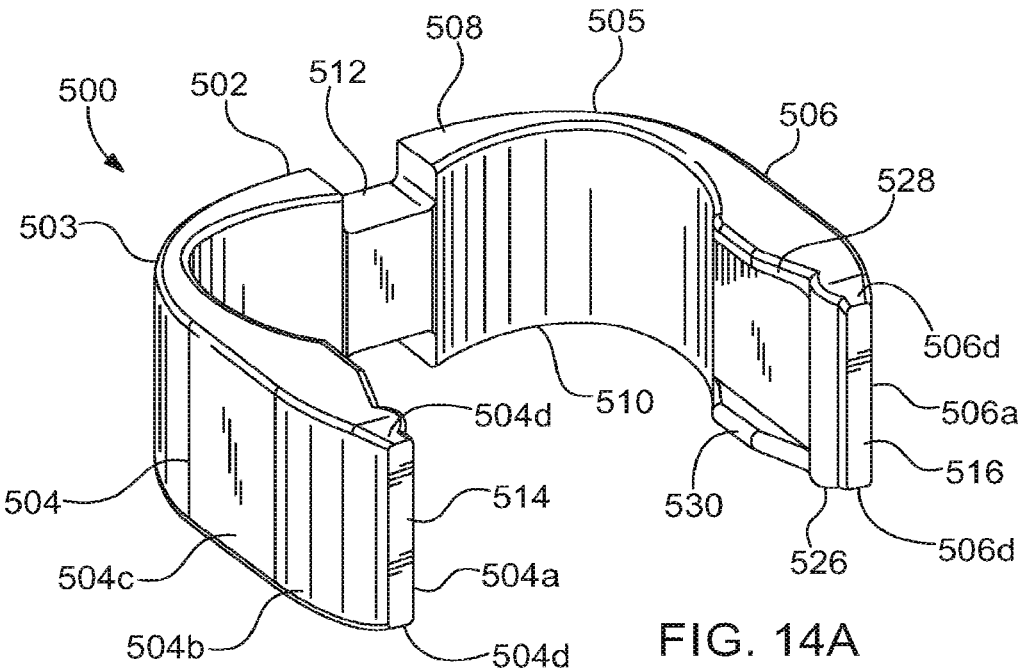
FIG. 14A is a perspective view of the second component, a modular shim, that, along with the cage shown in FIG. 13, forms an embodiment of the interbody spinal implant.
Figure 14B:
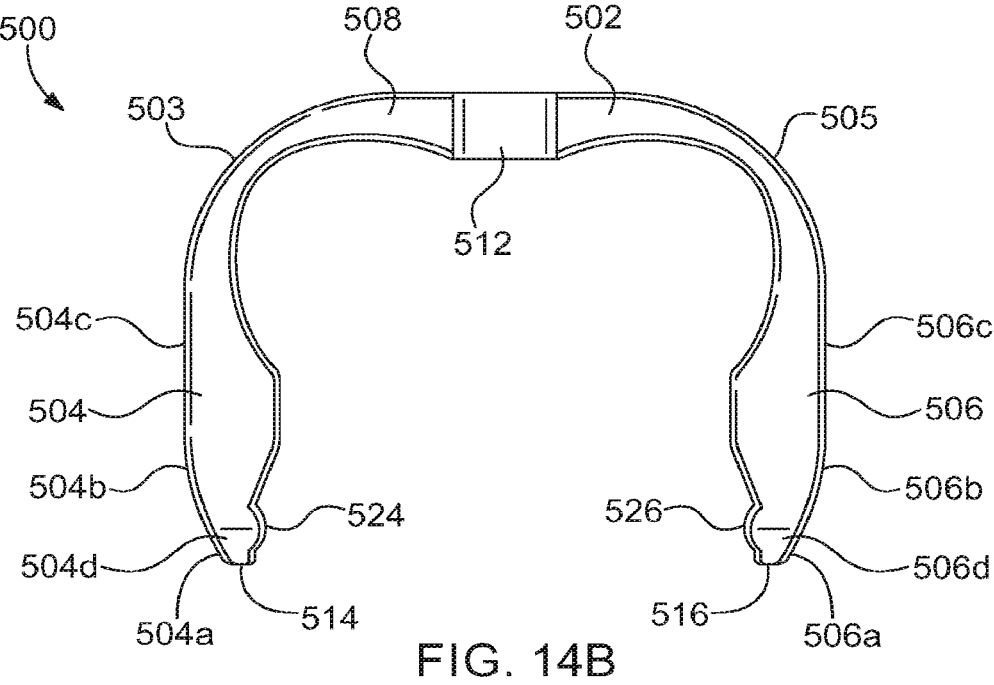
FIG. 14B is a top view of the shim shown in FIG. 14A.

FIG. 14A is a perspective view and FIG. 14B is a top view of the modular shim 500 that forms one of the components of the implant 301. As illustrated, the example embodiment of the shim 500 is substantially U-shaped, including a head 502; opposing side walls 504 and 506 each ending in a foot 504a and 506a; a top surface 508; and a bottom surface 510. The head 502 is connected to the opposing side walls 504 and 506 through a pair of corners 503 and 505, respectively. The corners 503, 505 are thinner than are either the head 502 or the side walls 504, 506 to facilitate flexing of the shim 500. Preferably, the shim 500 is an integral component. By "integral" is meant a single piece or a single unitary part that is complete by itself without additional pieces, i.e., the part is of one monolithic piece formed as a unit with another part.

The head 502 has a tool holding feature 512 which is preferably located centrally in the head 502. The tool holding feature 512 facilitates engagement with the tool 600, allowing the caretaker to hold, manipulate, and insert the shim 500 using the tool 600. The side wall 504 has an outside surface including a curved portion 504b proximate the foot 504a and a flat portion 504c proximate the corner 503. Similarly, the side wall 506 has an outside surface including a curved portion 506b proximate the foot 506a and a flat portion 506c proximate the corner 505.

Figure 14C:
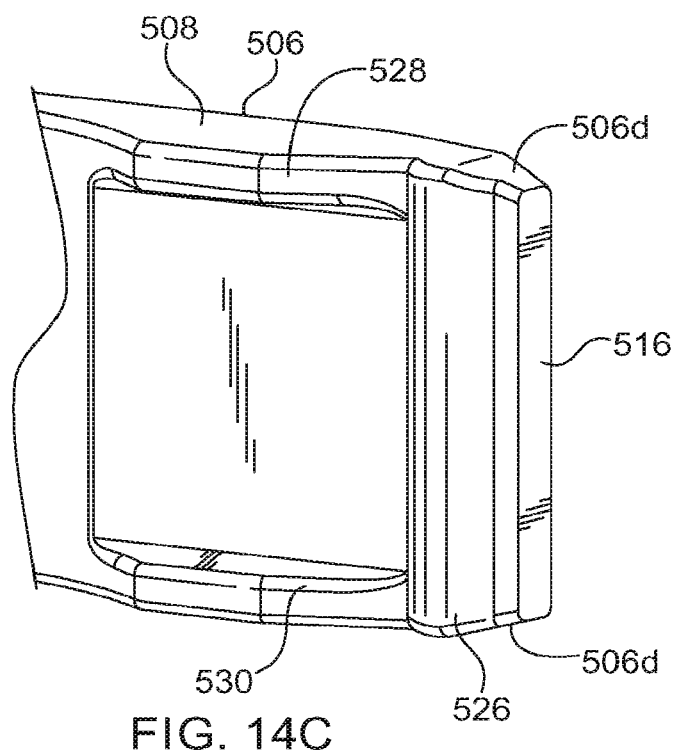
FIG. 14C is a partially cut-away view of the shim shown in FIGS. 14A and 14B.

As best shown in FIG. 14C, which is a partially cut-away view of the shim 500 highlighting the side wall 506 and the foot 506a, the foot 506a has a pair of lead-in chamfers 506d.

The side wall 504 and the foot 504a have similar chamfers 504d. The chamfers 504d, 506d slope downward from the top surface 508 toward the bottom surface 510 and upward from the bottom surface 510 toward the top surface 508. The chamfers 504d, 506d also taper inward from the outside surface toward the inside surface of the side walls 504, 506 and outward from the inside surface toward the outside surface of the side walls 504, 506. The chamfers 504d, 506d facilitate insertion by the caretaker of the shim 500 into engagement with the cage 400.

The chamfers 504d, 506d end at the flat distal faces 514 and 516, respectively, of the side walls 504 and 506. The terms "distal," "distal end," and "distal faces" are used to define the part or surface of a component which is facing the patient or positioned furthest from the user. The terms "proximal," "proximal end," and "proximal faces" are used to define the part or surface of a component which is facing away from the patient or positioned closest to the user. Thus, the head 502 forms the proximal face of the shim 500. The flat distal faces 514, 516 contact the stop 472 in the track 471 of the column 460 when the shim 500 is seated in the track 471, which prevents the flat distal faces 514, 516 of the shim 500 from contacting anatomical structures—thereby enhancing safety.

The foot 504a has a detent 524 and the foot 506a has a detent 526. The detents 524, 526 engage the final detent recess 452 of the track 451 of the body 440 of the cage 400 for final seating of the shim 500 in the track 451 of the body 440 and in the corresponding track 471 of the column 460, when the shim 500 fully engages the cage 400. Engagement between the detents 524, 526 and the final detent recess 452 is secured via a snap fit, enabled by the flexibility of both the corners 503, 505 and the material used to construct the shim 500. The detents 524, 526 can also engage the backup detent recess 453 of the track 451 to retain the shim 500 should the shim 500 become dislodged from the final detent recess 452.

On the respective inside surfaces of the side walls 504, 506 of the shim 500 are located an upper bracket 528 and a lower bracket 530. The upper bracket 528 aligns with and engages the track 451 of the body 440, and the lower bracket 530 aligns with and engages the track 471 of the column 460, when the shim 500 fully engages the cage 400. To prevent jamming upon engagement of the shim 500 with the body 440 and with the column 460, the chamfers 504d, 506d terminate, and the shim 500 is at its full height (following the slope and taper of the chamfers 504d, 506d}, before the upper bracket 528 and the lower bracket 530 begin.

As a component of the implant 301, the shim 500 can be made of the same durable material (described above) used to construct one or more of the components that combine to form the cage 400. The material used to construct the shim 500 could also be different from the durable material or materials used to construct the cage 400. The durable material used to construct the shim 500 must be flexible and resilient, however, to facilitate the snap-fit engagement of the shim 500 onto the cage 400. FIGS. 15 and 16 illustrate that snap-fit engagement.

Specifically, FIG. 15 shows the shim 500 aligned and poised for snap-fit engagement with the cage 400 to complete assembly of the implant 301. FIG. 16 illustrates the complete, assembled implant 301 with the shim 500 in position, and fully engaged with, the cage 400. During a surgical procedure, and using the tool 600, the caretaker places the cage 400 into position between vertebral bodies in a patient. Still using the tool 600, the caretaker extends or expands the cage 400, separating the body 440 from the column 460, until the top surface 421 of the first endplate 420 and the top surface 481 of the second endplate 480 forcibly press against anatomical structures. The cage 400 is essentially wedged into position, and appears as illustrated in FIG. 15, with the body 440 separated from the column 460 by a distance "D."

Using the tool 600, the caretaker places the shim 500 into the position shown in FIG. 15. The shim 500 is aligned with the body 440 and the column 460. More specifically, the flat distal faces 514, 516 of the shim 500 face both the track 451 of the body 440 and the track 471 of the column 460. The upper bracket 528 of the shim 500 aligns with the track 451 of the body 440 while the lower bracket 530 of the shim 500 aligns with the track 471 of the column 460.

The user then pushes the shim 500, still using the tool 600, in the direction of arrow "B" and into engagement with the cage 400. The chamfers 504d, 506d facilitate and ease initial engagement of the shim 500 with the tracks 451, 471 and between the body 440 and the column 460. A continued push of the shim 500 forces the shim into full engagement with the cage 400, as shown in FIG. 16. Such continued push causes the upper bracket 528 of the shim 500 to ride along the track 451 of the body 440 while the lower bracket 530 of the shim 500 rides along the track 471 of the column 460 until the detents 524, 526 snap into engagement with the final detent recess 452 of the body 440. Having assumed its final position and completed formation of the implant 301, the shim 500 maintains and fixes the separation distance D between the body 440 and the column 460 of the cage 400.

Figure 17:
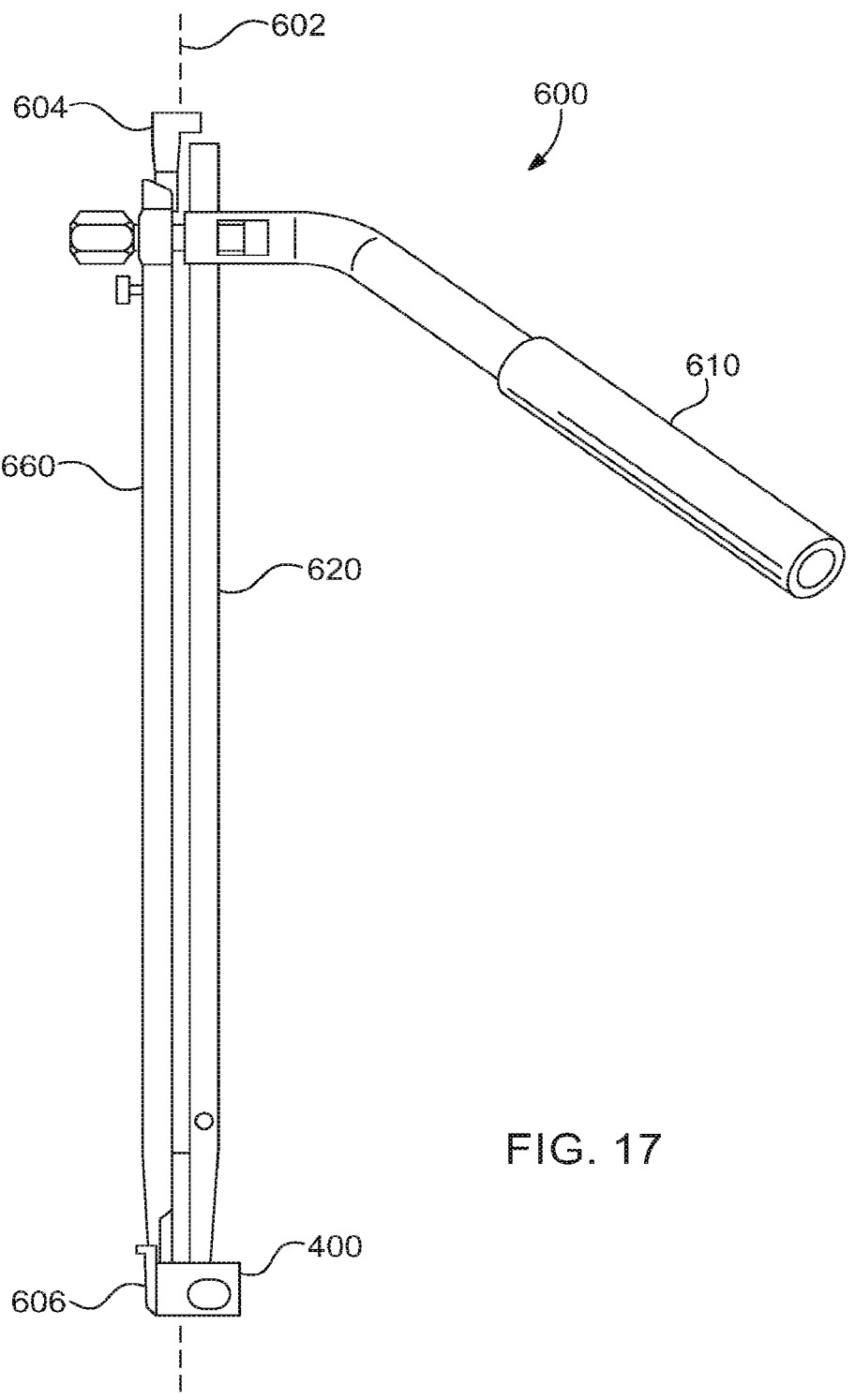
FIG. 17 shows an exemplary embodiment of the instrument or tool that, together with the implant shown in FIG. 16, form the components of a system according to the present invention, with the tool attached to the cage of the implant.

To facilitate manipulation and placement of the implant 301 by the caretaker, the instrument or tool 600 is provided. FIG. 17 shows an exemplary embodiment of the tool 600 that, together with the implant 301 shown in FIG. 16, form the components of a system 700 according to the present invention. As illustrated in FIG. 17, the tool 600 has a longitudinal axis 602 extending between a proximal end 604 and a distal end 606. The tool 600 includes an expander 620 designed to engage and manipulate the cage 400 and an inserter 660 designed to engage and manipulate the shim 500. The tool 600 also includes a side handle 610, which the caretaker uses to grasp and manipulate the tool 600.

Figure 18:
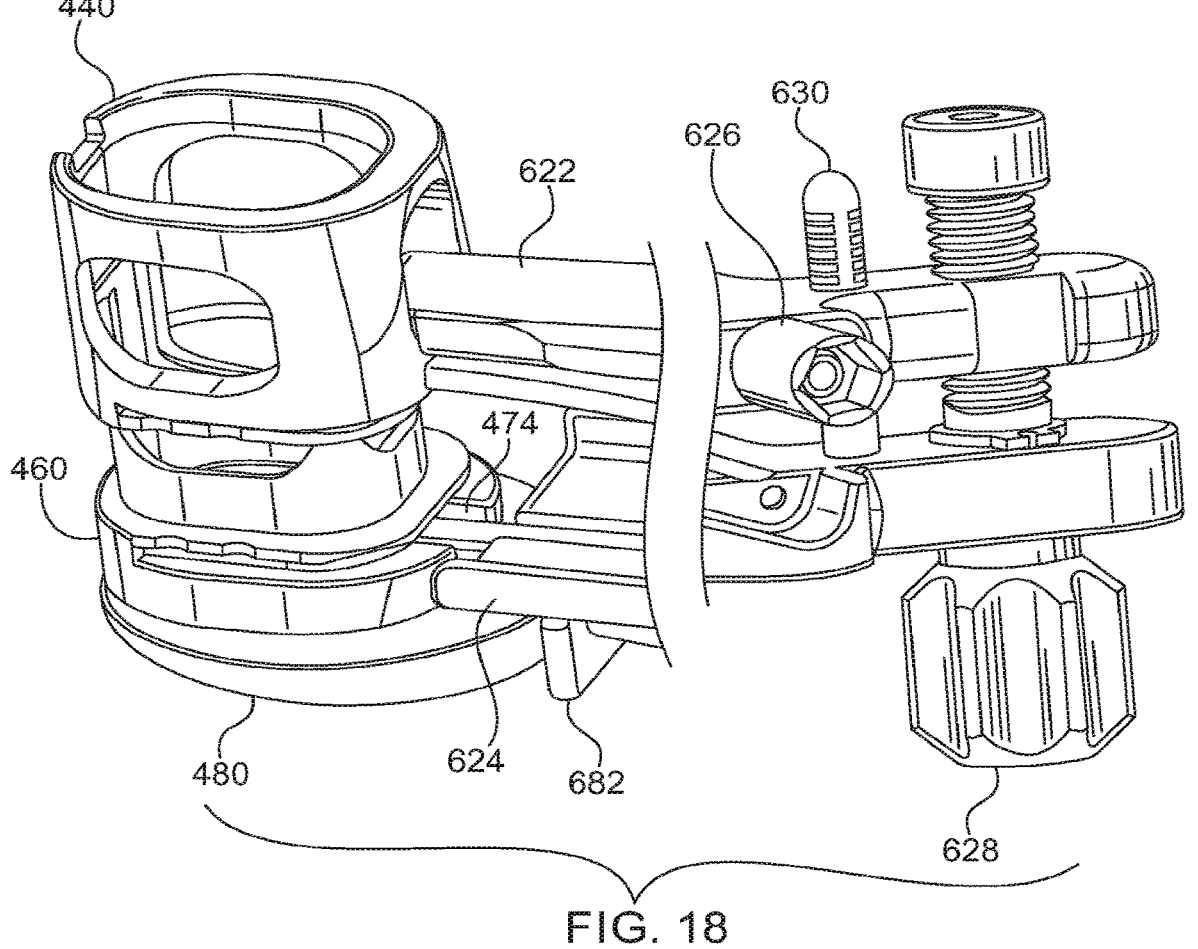
FIG. 18 shows the expander portion of the tool shown in FIG. 17 engaging and expanding the cage of the implant.

FIG. 18 shows the expander 620 of the tool 600 engaging the cage 400 of the implant 301. (The first endplate 620 of the cage 400 is removed for clarity in FIG. 18, but would ordinarily be positioned atop the body 440 as shown in FIG. 15.) The left-hand side of FIG. 18 highlights, in a cutaway view, the distal end of the expander 620 while the right-hand side of FIG. 18 highlights, in a cutaway view, the proximal end of the expander 620. At the distal end of the expander 620, a gripping member 622 engages the tool holding feature 454 of the body 440 of the cage 400. Also at the distal end of the expander 620, an actuator 624 engages the tool holding feature 474 of the column 460 of the cage 400.

The user can rotate the grip tightening knob 626 of the expander 620, which is located at the proximal end of the expander 620, to vary the engagement force between the expander 620 and the cage 400. Rotation of the grip tightening knob 626 in one direction (e.g., clockwise) tightens the grip or hold that the expander 620 exerts on the cage 400. Rotation of the grip tightening knob 626 in the opposite direction (e.g., counterclockwise) loosens the grip or hold that the expander 620 exerts on the cage 400.

The user will typically hold the tool 600 initially with one hand on the handle 610 and the other hand on the grip tightening knob 626. The user rotates the grip tightening knob 626 until the tool 600 firmly grasps and holds the cage 400. Once a firm engagement between the tool 600 and the cage 400 is secured, the user directs the cage 400 into position between vertebrae of the patient.

While still holding the handle 610 of the tool 600 with one hand, the user places the other hand on the expansion knob 628. Rotation of the expansion knob 628 in one direction (e.g., in the direction of the arrow labeled "EXPAND" in FIG. 18) causes the actuator 624 to separate the column 460 from the body 440 (i.e., to increase the distance "D" shown in FIG. 15). Consequently, the endplates 420, 480 push on respective vertebrae of the patient until the caretaker ascertains that the vertebral spacing is as desired for a particular surgical application. The caretaker then stops rotating the expansion knob 628.

Rotation of the expansion knob 628 in the opposite direction (e.g., in the direction opposite the arrow labeled "EXPAND" in FIG. 18) causes the actuator 624 to bring the column 460 closer to the body 440 (i.e., to decrease the distance "D" shown in FIG. 15). Thus, the caretaker can "fine tune" the distance between the column 460 and the body 440 by using the expansion knob 628. The expansion knob 628 is ratcheted to give the caretaker feedback throughout the process of expanding the space between the vertebrae. In addition, the expander 620 has an expansion gauge 630 with indications (e.g., a numerical scale, marked gradations, and the like) providing information to the user about the amount of expansion imparted by the expander 620 to the cage 400. Because the cage 400 is adjusted in situ, there is no (or, at least, reduced) need to maintain on hand either a variety of different sizes of cages 400 or trial cages (reducing inventory). In addition, the caretaker need only insert one cage 400, as opposed to trial cages, mistakenly sized cages, or both, thereby reducing the time of surgery and the risk of injury to the patient.

Once the cage 400 is in position between the vertebrae with the vertebrae separated as desired, the user selects an appropriately sized shim 500. The shim 500 should be sized to fit snugly between the body 440 and the column 460 of the cage 400 with the cage 400 in its expanded position between the vertebrae (and held in that position by the expander 620). The user then uses the inserter 660 to place the shim 500 into position on the cage 400 and complete formation of the implant 301 in situ.

Figures 19, 20, 21:
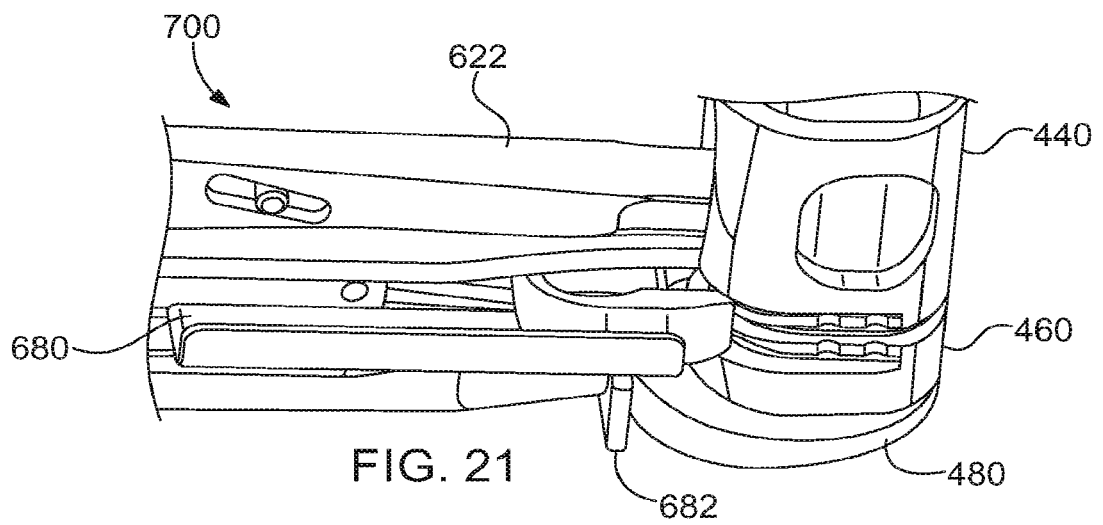
FIG. 19 shows the inserter portion of the tool shown in FIG. 17.
FIG. 20 shows the holding arms of the inserter shown in FIG. 19 holding the shim of the implant.
FIG. 21 illustrates the inserter portion of the tool shown in FIG. 20 inserting the shim into position on the cage with the cage expanded by the expander portion of the tool as shown in FIG. 18.

FIG. 19 shows the inserter 660 of the tool 600 shown in FIG. 17. The inserter 660 is connected to the tool 600 at a connection point 662 located proximate to a traveling knob 664. The inserter 660 has a holder actuator 666, located at the proximal end 604 of the tool 600, by which the user manipulates the inserter 660. The inserter 660 includes an elongated outer sleeve 670 that surrounds a pair of elongated arms 668. The arms 668 are configured to be translatable with respect to the sleeve 670 along the longitudinal axis 602. More specifically, the arms 668 slide within the sleeve 670. Thus, the arms 668 can both be extended from and be retracted into the sleeve 670 by actions of the user.

The caretaker can grasp the holder actuator 666 comfortably and easily in one hand to hold and manipulate the inserter 660 and, ultimately, the shim 500. While still holding the handle 610 of the tool 600 with one hand, the caretaker places the other hand on the holder actuator 666. The caretaker uses the holder actuator 666 to manipulate the arms 668 into position engaging the tool holding feature 512 of the shim 500. FIG. 20 illustrates the arms 668 of the inserter 660 shown in FIG. 19 holding the shim 500 of the implant 301. The caretaker can then use the holder actuator 666 to translate the arms 668 with respect to the sleeve 670 and towards the cage 400. In turn, that action moves the shim 500 toward the cage 400.

FIG. 21 illustrates the inserter 660 of the tool 600 inserting the shim 500 into position on the cage 400, and between the body 440 and the column 460, with the cage 400 expanded by the expander 620 of the tool 600. The tool 600 has a guide 680 which assures that the shim 500 moves toward the cage 400 in an aligned orientation. The tool 600 also has a stop plate 682 that can abut the flat portion 484 of the endplate 480 to stabilize the tool 600 against the cage 400 and prevent the cage 400 from moving in the posterior direction.

Some of the important features of the implant 301 include modular components 420, 440, 460, 480, 500 with friction fit and snap fit engagements; modular endplates 420, 480 for different footprints and lordosis; an adjustable expansion mechanism that retains graft material; tracks 451, 471 for locking the shim 500 and (if any) shim trials; and a keyed fit for orientation. Further features include retention barbs 425, 485 for fixation; double detent recesses 452, 453 to prevent the shim 500 from dislodging; an interior window for post-packing of graft material; and a roughened topography 380 to facilitate integration. The tool 600 allows for insertion, expansion, trialing, and seating of the cage 400 and shim 500. The implant 301 can be used in lumbar or thoracic corpectomy. In addition, the modular and expanding mechanisms can be used for other medical implants, such as an adjustable hip stem.

In summary, the system 700 for inserting the implant 301, typically but not necessarily using a cervical fusion procedure, has two components: the implant 301 and the tool 600. The implant 301 combines the modular cage 400 and the shim 500. The tool 600 combines the expander 620 and the inserter 660. Having described the components of the system 700, an exemplary method by which a caretaker might use the system 700 follows.

During the method of using the system 700, the caretaker will first identify or diagnose a spinal disc in need of repair or replacement. The caretaker next performs at least a partial discectomy, either removing or creating a channel in the affected vertebral body or bodies, in the usual manner. The caretaker then assesses or gauges the appropriate size of implant 301 to insert into the disc space (via measurement using a caliper or other device, a trial implant, or another technique known in the art) created by the discectomy. Such assessment of the required height for the implant 301 instructs the caretaker which modular components to collect and assemble to create an implant 301 with a shorter than required height (to allow for expansion) and an ideal lordosis and footprint.

FIGS. 9, 13, 17, 18, 19, and 21 illustrate the various steps in the method by which the caretaker typically manipulates the tool 600 and the implant 301 when the application is a cervical fusion procedure. FIG. 9 illustrates the starting position, in which the caretaker has collected the four modular components (the first endplate 420, the body 440, the column 460, and the second endplate 480) that will form the cage 400 of the implant 301 having a size and shape suitable for the disc space created by the discectomy. After collecting those components, the caretaker assembles them together. FIG. 13 illustrates the cage 400 with its four modular components assembled or engaged. Bone graft material (not shown) is then optionally inserted into the internal cavity of the implant 301 defined by the vertical aperture 426, 447, 467, 486.

FIG. 17 illustrates the next step in the method, in which the caretaker couples the cage 400 to the expander 620 of the tool 600. The caretaker will typically orient the cage 400 to the tool 600 as shown in FIG. 17 when coupling the cage 400 to the expander 620. Next, while grasping the handle 610 of the tool 600, the caretaker inserts the cage 400 of the implant 301 into the disc space created during the discectomy procedure. Given the modular and adjustable characteristics of the cage 400, it is not necessary to distract the adjacent vertebral bodies when inserting the cage 400—an advantage over conventional implants. Rather, the cage 400 will be shorter than the final height required to separate the vertebrae.

The caretaker manipulates both the handle 610 and the actuator 624 of the expander 620 until the optimum final positioning of the cage 400 is achieved with respect to the disc space. The insertion steps can be facilitated while viewing the position of the cage 400 if either markers are provided on the cage 400, which can be seen (for example} under fluoroscopic imaging, or X-rays are taken. Such markers, X-rays, or both can help the caretaker to determine the precise position of the cage 400 with respect to the disc space.

Once the cage 400 is located in its final position, the caretaker adjusts (i.e., expands} the cage 400, using the expander 620 to separate the body 440 from the column 660, as illustrated in FIG. 18 and described above. The cage 400 is adjusted (expanded} until the adjacent vertebral bodies are distracted by the requisite amount as determined by the caretaker. The cage 18 is now in its final position and at its final height between the vertebrae.

FIG. 19 illustrates the next step in the method, in which the caretaker (after selecting a shim 500 that corresponds in size to the distance "D," shown in FIG. 15, between the body 440 and the column 660 with the cage 400 in its final position and at its final height} couples the shim 500 to the inserter 660 of the tool 600. The caretaker will typically orient the shim 500 to the tool 600 as shown in FIGS. 19 and 20 when coupling the shim 500 to the inserter 660. Next, while grasping the handle 610 of the tool 600, the caretaker inserts the shim 500 of the implant 301 into the disc space.

Insertion of the shim 500 continues, as illustrated in FIG. 21, until the shim 500 is in position on the cage 400 and between the body 440 and the column 460 with the cage 400 expanded by the expander 620 of the tool 600. If the shim 500 is determined to lack the optimum size, the caretaker can retract the shim 500 and insert a differently sized shim 500. The caretaker can repeat these steps until the shim 500 fits as desired. Once the ideal height shim 500 is determined, the shim 500 is inserted until flush with the cage 400 and is locked into engagement on the cage 500—thereby completing formation of the implant 301 in situ.

The caretaker can then release the arms 668 of the inserter 660 from the shim 500 and retract the inserter 660 from the disc space, leaving the shim 500 in position. The caretaker than rotates the expansion knob 628 so that the actuator 624 moves closer to the gripping member 622, allowing the caretaker to retract the expander 620 from the disc space, leaving the cage 400 in position. The compression forces between the vertebral bodies and the top surfaces 421,481 of the first and second endplates 420,480 of the implant 301 maintain the implant 301 in place as the caretaker removes the tool 600 from the disc space and from the body of the patient.

Imaging or X-rays can ascertain for the caretaker that the implant 301 is located precisely and correctly in its final position. The vertical aperture 426, 447, 467, 486 and transverse aperture 448, 468 can be viewed using lateral and/or frontal X-rays, for example, to confirm the appropriate position of the implant 301 within the disc space. Throughout the entirety of the insertion process, the angle and position of the tool 600 with respect to the disc space can be maintained substantially constant; the actions performed by the caretaker to articulate the cage 400 and shim 500 that form the implant 301 do not require movement of the tool 600.

The spinal implant 301 and the associated tool 600, and the related method of using the system 700, improve the ease with which the implant 301 may be manipulated during insertion or once within the disc space. The implant 301, tool 600, and method keep the insertion width of the system 700 smaller and enable the caretaker to manipulate the implant 301 within the disc space, in situ, without passing multiple instruments by the exposed nerve roots. The system 700 avoids the need for a large incision and subsequent trauma to the spine, as well as reduces the risk of damaging the nerve root with multiple passes of instrumentation.

Figure 22:
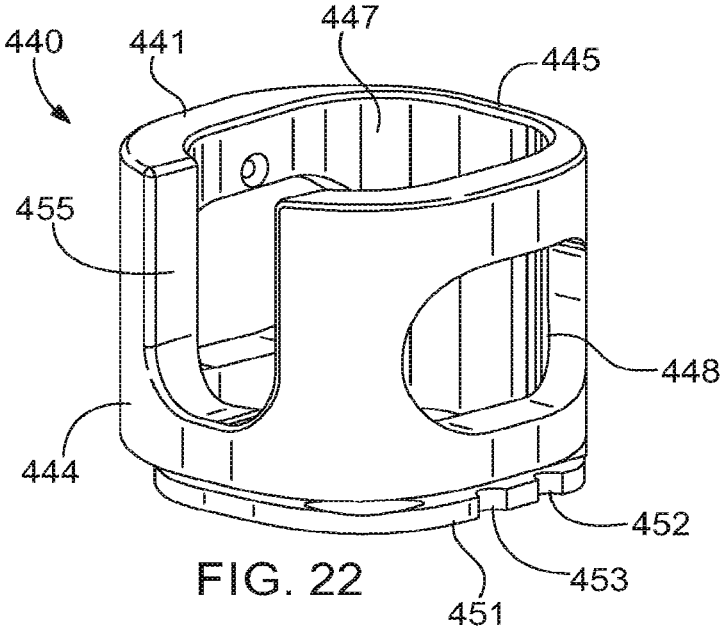
FIG. 22 illustrates an alternative embodiment of the body shown in FIG. 10.
Figure 23:
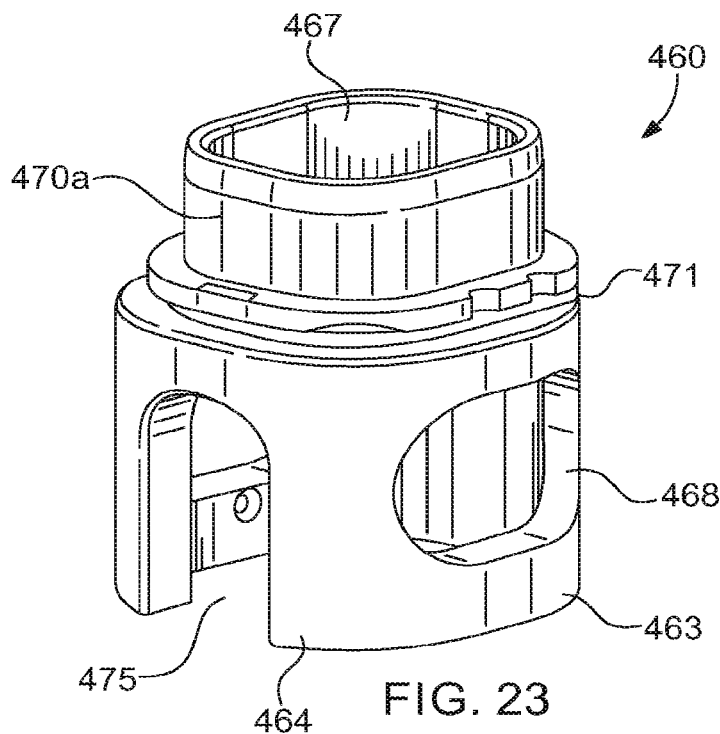
FIG. 23 illustrates an alternative embodiment of the column shown in FIG. 11.
Figure 24:
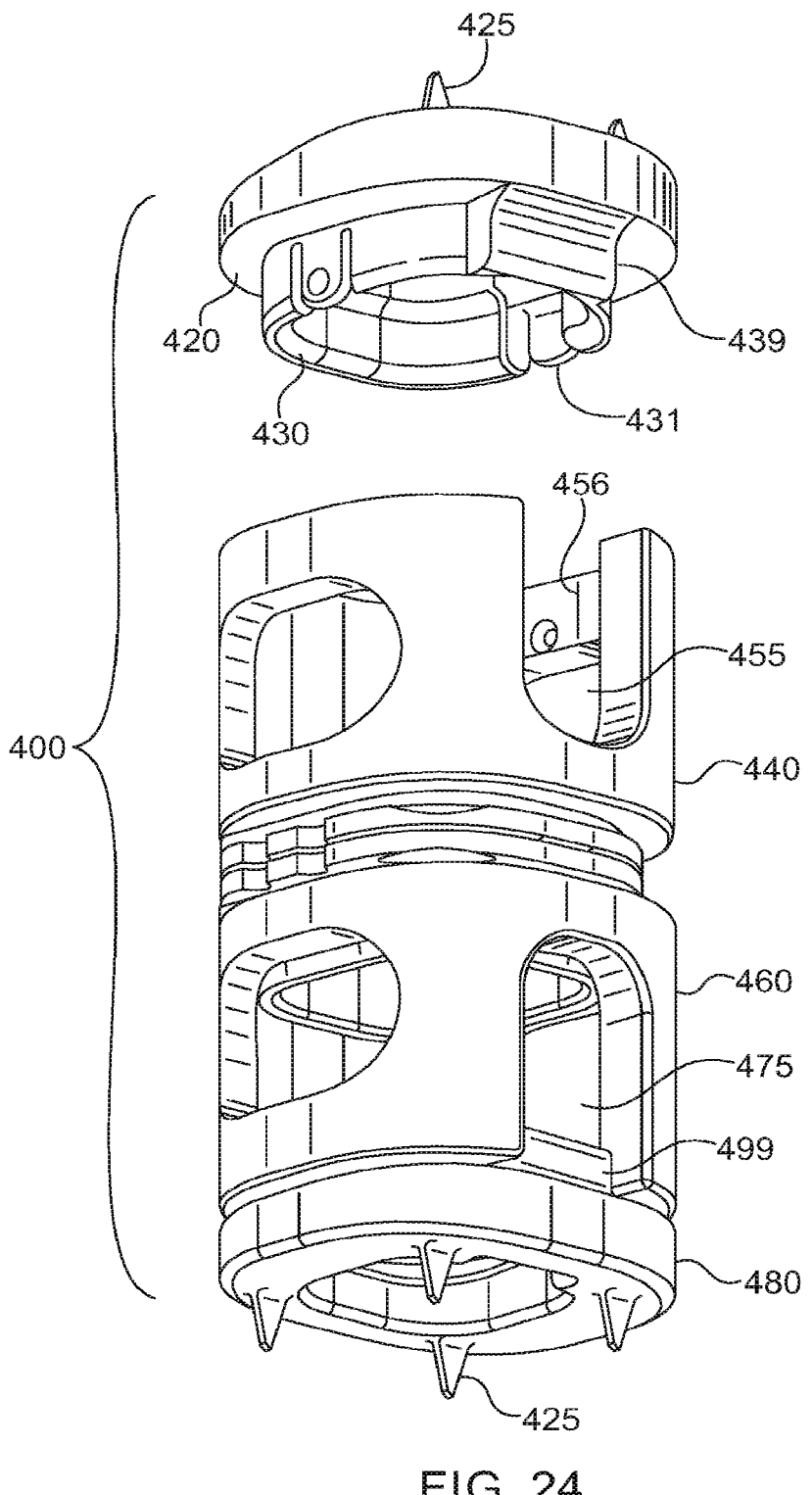
FIG. 24 illustrates alternative embodiments of the first endplate and the second endplate, with the body and the column shown in FIGS. 22 and 23, respectively, assembled together and engaged fully, the second endplate assembled together and engaged with the column, and the first endplate unassembled, not yet engaged with the body, and, therefore, highlighted.
Figure 25:
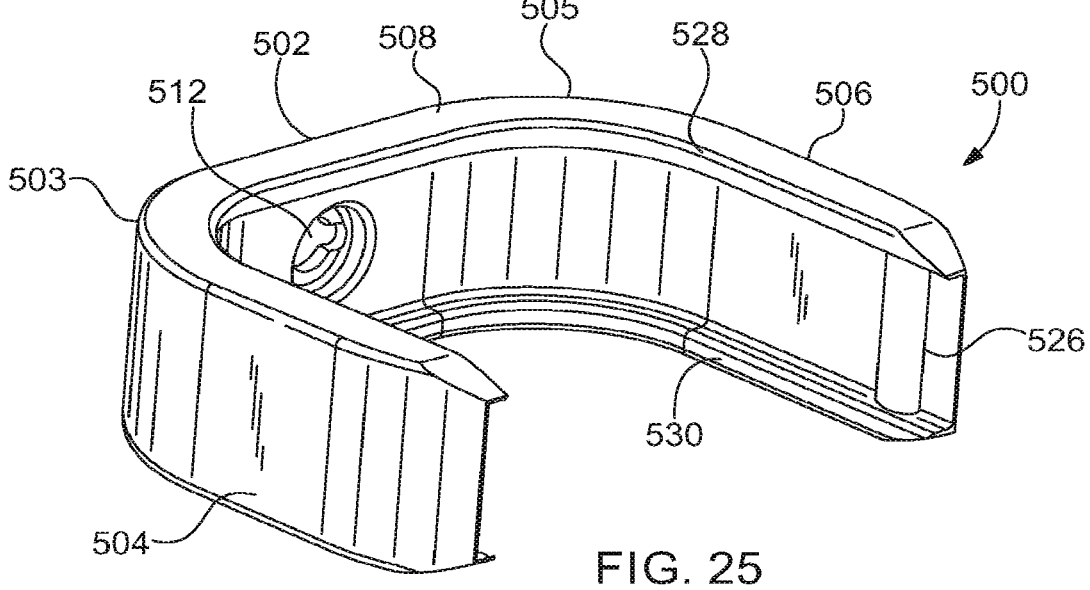
FIG. 25 illustrates an alternative embodiment of the shim shown in FIG. 14A.
Figure 26:
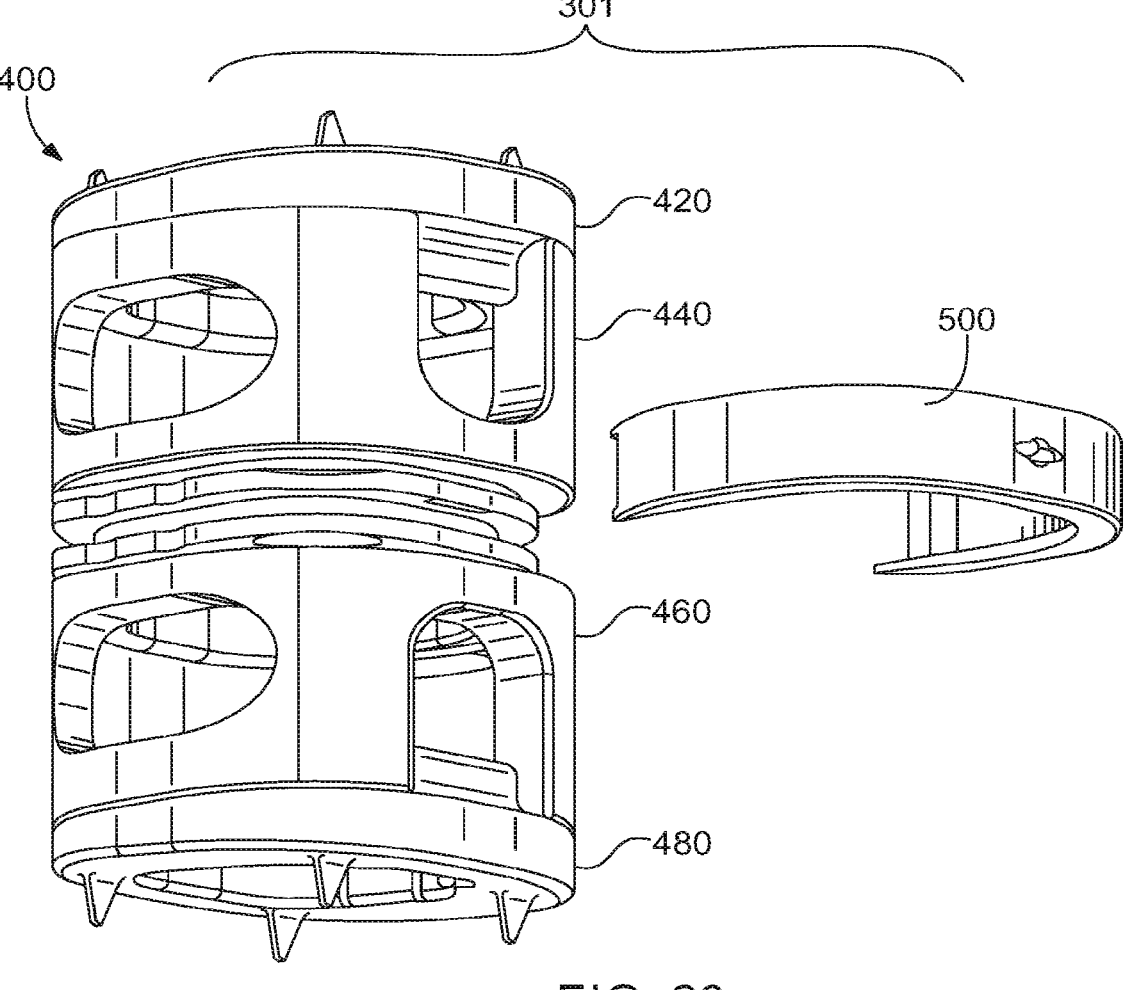
FIG. 26 illustrates the shim shown in FIG. 25 aligned and poised for engagement with the cage shown in FIG. 24 to complete assembly of an embodiment of the interbody spinal implant.
Figure 27:
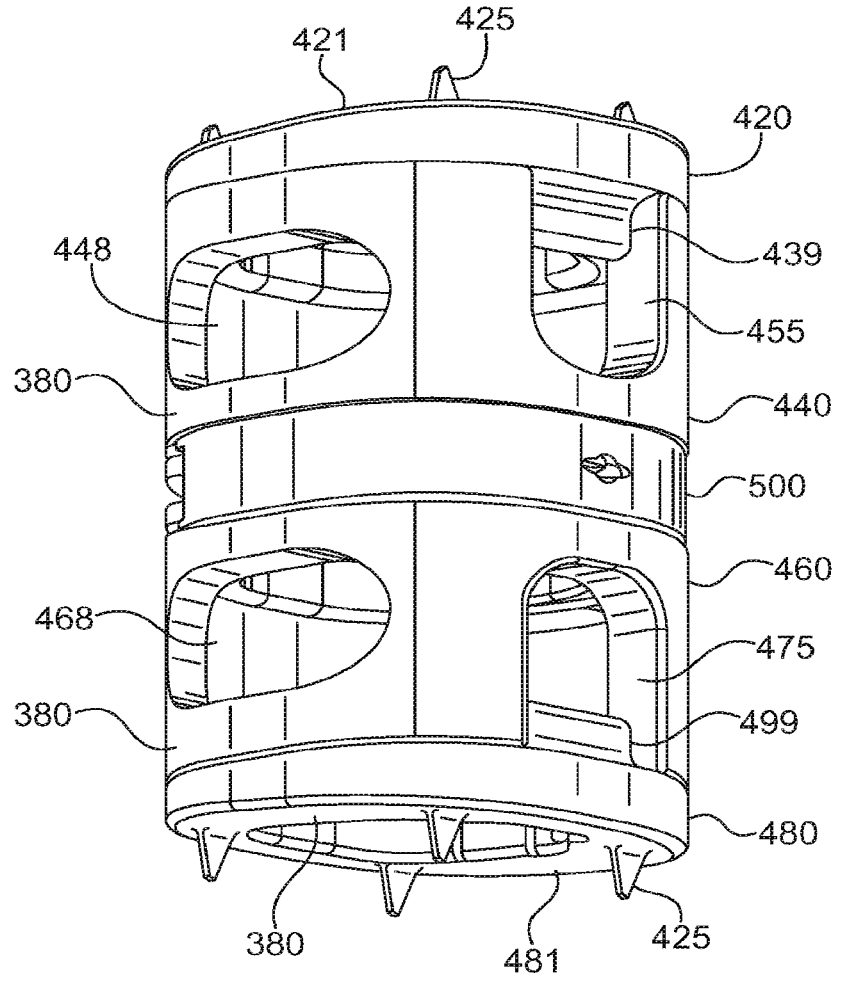
FIG. 27 illustrates the cage and shim shown in FIG. 26 as fully engaged, thereby completing assembly of an embodiment of the interbody spinal implant.

FIGS. 22 through 27 illustrate an alternative embodiment of the cage 400 and shim 500 that combine to form the implant 301. More specifically, FIG. 22 illustrates an alternative embodiment of the body 440 shown in FIG. 10; FIG. 23 illustrates an alternative embodiment of the column 460 shown in FIG. 11; FIG. 24 illustrates alternative embodiments of the first endplate 420 and the second endplate 480, with the body 440 and the column 460 (shown in FIGS. 22 and 23, respectively} assembled together and engaged fully, the second endplate 480 assembled together and engaged with the column 460, and the first endplate 420 unassembled, not yet engaged with the body 440, and, therefore, highlighted; FIG. 25 illustrates an alternative embodiment of the shim 500 shown in FIG. 14A; FIG. 26 illustrates the shim 500 shown in FIG. 25 aligned and poised for engagement with the cage 400 shown in FIG. 24 to complete assembly of an embodiment of the interbody spinal implant 301; and FIG. 27 illustrates the cage 400 and shim 500 shown in FIG. 26 as fully engaged, thereby completing assembly of an embodiment of the interbody spinal implant 301.

Many of the features of the embodiment of the implant 301 disclosed above in connection with FIGS. 9-16 are the same as the features of the embodiment of the implant 301 disclosed in connection with FIGS. 22-27. There are also significant differences, however, between the embodiments. For example, the embodiment of the body 440 illustrated in FIG. 22 does not have the transition portion 446, the same key slot 449, or the same tool holding feature 454 as the embodiment of the body 440 illustrated in FIG. 10.

Most notably, the embodiment of the column 460 illustrated in FIG. 23 does not have the legs 470 of the embodiment of the column 460 illustrated in FIG. 11. The discrete legs 470 have been replaced by a single, substantially square-shaped, fully enclosed leg 470a, which engages the body 440 in a manner similar to the legs 470. Whether having the discrete legs 470 or the single leg 470, however, both embodiments allow the user to expand or adjust the height of the implant 301 continuously (rather than incrementally) in situ, by sliding the body 440 along the legs 470 or the leg 470. Thus, the implant 301 can assume a potentially infinite number of possible heights between a starting height (where the body 440 is fully seated on the column 460) and an upper limit {where the body 440 exceeds the height of the legs 470 or leg 470 and, therefore, the body 440 no longer contacts the column 460).

FIG. 24 highlights a difference in the seat 430 between the embodiments of the first endplate 420 and the second endplate 480 shown in FIG. 24 and the corresponding components disclosed earlier. As shown in FIG. 24, the seat 430 has a flexible member 431 that engages, via a snap fit, a corresponding catch 456 on the body 440 and on the column 460 of the cage 400 when the first endplate 420 engages the body 440 and when the second endplate 480 engages the column 460. Also illustrated in FIG. 24 is an alternative embodiment of the key slot 449 disclosed on the body 440 for the embodiment above; the endplates 420 and 480 of the embodiment shown in FIG. 24 each have a ledge 439 and 499, respectively. The ledge 439 orients the first endplate 420 with respect to the body 440 via engagement with the anterior window 455, enabling the user to place the first endplate 420 on the body 440 easily. The ledge 499 orients the second endplate 480 with respect to the column 460 via engagement with the anterior window 475, enabling the user to place the second endplate 480 on the column 460 easily.

FIG. 25 highlights an important difference between the embodiment of shim 500 shown in FIG. 25 and the embodiment of the shim 500 shown in FIG. 14A. The tool holding feature 512 of the earlier embodiment had a substantially H-shaped configuration, suitable for engagement by the arms 668 of the tool 600. In contrast, the tool holding feature 512 of the embodiment shown in FIG. 25 has a circular, threaded configuration, suitable for engagement by a correspondingly threaded instrument {not shown, but within the skill of an artisan).

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. It is also expressly intended that the steps of the methods of using the various devices disclosed above are not restricted to any particular order.

The invention claimed is:

1. A system for use during a surgical procedure on a patient, the system comprising:

an implant having a modular cage and a shim comprising a side wall having a top surface, a bottom surface, an inside surface, and an outside surface, wherein the shim comprises:

at least one bracket on the inside surface, a first tool holding feature on the top surface, and a second tool holding feature on the bottom surface, and the modular cage comprising:

a first endplate adapted to press against anatomical structures of the patient, a second endplate adapted to press against opposing anatomical structures of the patient, a body with a top body surface on which the first endplate is positioned and a first track extending along more than one side of the body, and a column with a bottom column surface on which the second endplate is positioned, a second track extending along more than one side of the column, wherein the column comprises at least one leg over which the body slides so that the at least one leg is contained at least partially within the body; and wherein the at least one bracket facilitates alignment of the shim with the modular cage, wherein the at least one bracket is configured to engage the first track, the second track, or both and secure to the first track, the second track, or both, via a snap fit; and wherein the system comprises a tool having an expander and an inserter, the tool engaging a cage tool holding feature on the modular cage and adapted to position the modular cage at a surgical site within the patient, the expander sliding the body along the at least one leg to separate the body from the column in situ and thereby define the height of the implant, and the inserter positioning the shim between the body and the column.

2. The system of claim 1, wherein the at least one bracket is at least two brackets, and wherein the at least two brackets are disposed on the inside surface.

3. The system of claim 1, wherein the more than one side of the body comprises two opposing lateral sides, and wherein the at least one bracket is at least two brackets, and wherein the at least two brackets are configured to engage the first track and the second track via the snap fit along the two opposing lateral sides.

4. The system of claim 1, wherein the height of the implant can be adjusted in situ to any number of possible heights between a starting height where the body is fully seated on the column and an upper limit where the body exceeds the height of the at least one leg, and the shim when positioned between the body and the column fixes the distance between the body and the column.

5. The system of claim 1, wherein the shim comprises a plurality of chamfers disposed at ends of the shim.

6. The system of claim 5, wherein the plurality of chamfers taper away from the at least one bracket.

7. The system of claim 5, wherein the plurality of chamfers end before the at least one bracket begins along the side wall of the shim.

8. The system of claim 1, wherein the at least one bracket is configured to ride along the first track, the second track, or both, while the shim is in an engagement position with the modular cage.

9. The system of claim 1, wherein the first track of the body has a detent recess for seating the at least one bracket of the shim under a chamfer of the first track and in the first track.

10. The system of claim 9, wherein the shim comprises a detent that engages the detent recess of the body for seating of the shim.

11. The system of claim 1, wherein the first track, the second track, or both, comprise a flange having an undercut and a lead-in chamfer to facilitate insertion of the lower bracket of the shim.

12. The system of claim 1, wherein the inside surface of the side wall is configured to contact the first track, the second track or both, while the at least one bracket engages the first track, the second track, or both.

13. The system of claim 1, wherein the first tool holding feature comprises a first recess along the top surface, and wherein the second tool holding feature comprises a second recess along the bottom surface.

14. The system of claim 1, wherein the first tool holding feature and the second tool feature are configured to facilitate translation of arms of the tool in a direction towards the modular cage.

15. A system for use during a surgical procedure on a patient, the system comprising:

an implant having a modular cage and a shim comprising a side wall having a top surface, a bottom surface, an inside surface, and an outside surface, wherein the shim comprises:

at least one bracket on the inside surface,
a first tool holding feature on the top surface, and
a second tool holding feature on the bottom surface, and the modular cage comprising:

a first endplate adapted to press against anatomical structures of the patient,
a second endplate adapted to press against opposing anatomical structures of the patient,
a body with a top body surface on which the first endplate is positioned and a first track extending along at least the lateral sides of the body, and
a column with a bottom column surface on which the second endplate is positioned,
a second track extending along at least the lateral sides of the column, wherein the column comprises at least one leg over which the body slides so that the at least one leg is contained at least partially within the body; and wherein the at least one bracket facilitates alignment of the shim with the modular cage, wherein the at least one bracket is configured to engage the first track, the second track, or both and secure to the first track, the second track, or both, via a snap fit; and wherein the system comprises a tool having an expander and an inserter, the tool engaging a cage tool holding feature on the modular cage and adapted to position the modular cage at a surgical site within the patient, the expander sliding the body along the at least one leg to separate the body from the column in situ and thereby define the height of the implant, and the inserter positioning the shim between the body and the column.

16. The system of claim 15, wherein the first track, the second track, or both extend continuously between lateral sides of the body, the column, or both.

17. The system of claim 15, wherein the at least one bracket is at least two brackets, and wherein the at least two brackets are disposed on the inside surface.

18. The system of claim 15, wherein the side wall is configured to at least partially surround the first track and the second track, and wherein the at least one bracket extends inwardly from the side wall.

19. The system of claim 15, wherein the at least one bracket is a first bracket and a second bracket, wherein the first bracket is configured to engage the first track, and wherein the second bracket is configured to engage the second track.

20. The system of claim 15, wherein the modular cage comprises four modules, the four modules are the first endplate, the second endplate, the body, and the column.

* * * * *